(12) United States Patent
Zheng

(10) Patent No.: US 11,535,628 B2
(45) Date of Patent: Dec. 27, 2022

(54) METHOD FOR PREPARATION OF ASENAPINE

(71) Applicant: ZHEJIANG AUSUN PHARMACEUTICAL CO., LTD., Linhai (CN)

(72) Inventor: Zhiguo Zheng, Linhai (CN)

(73) Assignee: ZHEJIANG AUSUN PHARMACEUTICAL CO., LTD., Linhai (CN)

( * ) Notice: Subject to any disclaimer, the term of this patent is extended or adjusted under 35 U.S.C. 154(b) by 0 days.

(21) Appl. No.: 16/992,961

(22) Filed: Aug. 13, 2020

(65) Prior Publication Data

US 2021/0047339 A1   Feb. 18, 2021

(30) Foreign Application Priority Data

Aug. 13, 2019 (CN) .......................... 201910744003.9

(51) Int. Cl.
*C07D 491/044* (2006.01)

(52) U.S. Cl.
CPC ...... *C07D 491/044* (2013.01); *C07B 2200/13* (2013.01)

(58) Field of Classification Search
CPC ............................................... C07D 491/044
See application file for complete search history.

(56) References Cited

U.S. PATENT DOCUMENTS

| 4,145,434 | A  | 3/1979 | Van Der Burg |
| 7,750,167 | B2 | 7/2010 | Kemperman et al. |

FOREIGN PATENT DOCUMENTS

| CN | 102229613    | 11/2011 |
| CN | 104974167    | 10/2015 |
| CN | 104974168    | 10/2015 |
| CN | 107759609 A  | 3/2018  |
| KR | 20150107357 A | 9/2015 |
| WO | WO 2008/003460 | 1/2008 |
| WO | WO 2012/040845 | 4/2012 |
| WO | WO 2013/061247 | 5/2013 |

OTHER PUBLICATIONS

Registry No. 2407041-33-0; 2407041-31-8, 2407041-30-7; 2407041-17-0, File REGISTRY on STN, entered STN Jan. 14, 2020.*
CN102229613, GrowingChen Co. Ltd., "New Process for Synthesis of Asenapine," Nov. 2, 2011, English language machine translation of abstract, Espacenet, date obtained: Nov. 13, 2020, 1 page.
CN104974167, Yangpu HG Pharmaceutical Co. Ltd., "Preparation Method of Asenapine and Intermediate Used for Preparing Asenapine," Oct. 14, 2015, English language machine translation of abstract, Espacenet, date obtained: Nov. 13, 2020, 1 page.
CN104974168, Yangpu HG Pharmaceutical Co. Ltd., "Preparation Method of Asenapine and Intermediate Used for Preparing Asenapine," Espacenet, date obtained: Nov. 13, 2020, 1 page.
CN107759609a, Tianjin Hankang Pharmaceutical Biotechnology Co. Ltd., "Purification Method of Asenapine," Mar. 6, 2018, English language machine translation of abstract, Espacenet, date obtained: Aug. 16, 2021, 1 page.
KR20150107357a, Kuhnil Pharm Co. Ltd., "Process for Preparing 8-Hydroxyclomipramine or its Pharmaceutically Acceptable Salt," Sep. 23, 2015, English language machine translation of abstract, Espacenet, date obtained: Aug. 16, 2021, 1 page.
Vader. J. et al., "The Syntheses of Radiolabelled Org 5222 and Its Main Metabolite Org 30526," Journal of Labelled Compounds and Radiopharmaceuticals, 1994, vol. 34, No. 9, 845-869.
Linden, "Debottlenecking the Synthesis Route of Asenapine," Organic Process Research & Development, 2008, 12(2), 196-201.
Zheng et al., "Strategy for Overcoming Full Reversibility of Intermolecular Radical Addition to Aldehydes: Tandem C-H and C-O Bonds Cleaving Cyclization of (Phenoxymethyl)arenes with Carbonyls to Benzofurans," Organic Letters, American Chemical Society, 2018, vol. 20, pp. 3310-3313.
Zhigang, "Section 11.3. Diazonium Compound and Application Thereof," Organic Chemistry, Henan Science and Technology Press, 2010, pp. 318-323.

* cited by examiner

*Primary Examiner* — Rebecca L Anderson
(74) *Attorney, Agent, or Firm* — Hoxie & Associates LLC

(57) ABSTRACT

The present invention relates to a method for preparing Asenapine. In particular, the present invention relates to a method for preparing pharmaceutically acceptable Asenapine free base and new crystal form thereof, and also relates to methods for preparing the intermediate compounds used in said method.

9 Claims, 3 Drawing Sheets

METHOD FOR PREPARATION OF ASENAPINE

CROSS-REFERENCE TO RELATED APPLICATIONS

The present application is a U.S. non-provisional application which claims priority to Chinese Application No. 201910744003.9, filed on Aug. 13, 2019, the entire contents of which are incorporated herein by reference for all purposes.

FIELD OF THE INVENTION

The present invention relates to the field of synthesis of organic compounds. In particular, the present invention relates to a method for preparing the antipsychotic drug Asenapine, i.e., the compound trans-5-chloro-2-methyl-2,3,3a,12b-tetrahydro-1H-dibenzo[2,3:6,7]-oxepino[4,5-c]pyrrole, and new crystal form thereof.

BACKGROUND OF THE INVENTION

Asenapine refers to the compound trans-5-chloro-2-methyl-2,3,3a,12b-tetrahydro-1H-dibenzo[2,3:6,7]-oxepino[4,5-c]pyrrole. Its maleate salt can be used for the emergent treatment of adult schizophrenia, mania or mixed type I bipolar disorder. The mechanism of action of Asenapine may be related to the antagonism of dopamine D2 and serotonin 2A. It is suitable to be used for treating manic or mixed episodes of schizophrenia and type I bipolar disorder, and has good antipsychotic effects. At present, antipsychotic drugs have become the fifth largest treatment category after cholesterol-lowering drugs, and are sold in the global market with market scale of 16.2 billion US dollars. In China, the antipsychotic drug market maintains compound annual growth rate of more than 40%, and the market share of anti-schizophrenic drugs is about 30%, which is growing at an average annual growth rate of 9.8%. Therefore, it is necessary to research and develop a new preparation method of asenapine suitable for industrial production.

Up to now, there are many literatures and patents reporting the synthesis of Asenapine. At first, the U.S. Pat. No. 4,145,434 and the literature (Vader, J.; Kaspersen, F.; Sperling, E.; Schlachter, I.; Terpstra, A.; Hilberink, P.; Wagenaars, G. J. Labelled Compd. Radiopharm. 1994, 34, 845-869.) reported the method for preparing Asenapine, respectively. Its synthetic route is as follows:

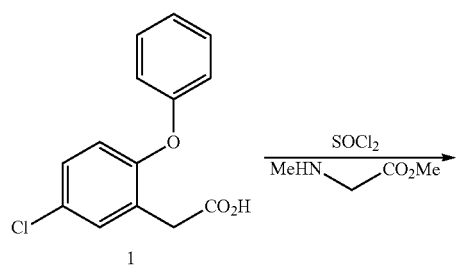

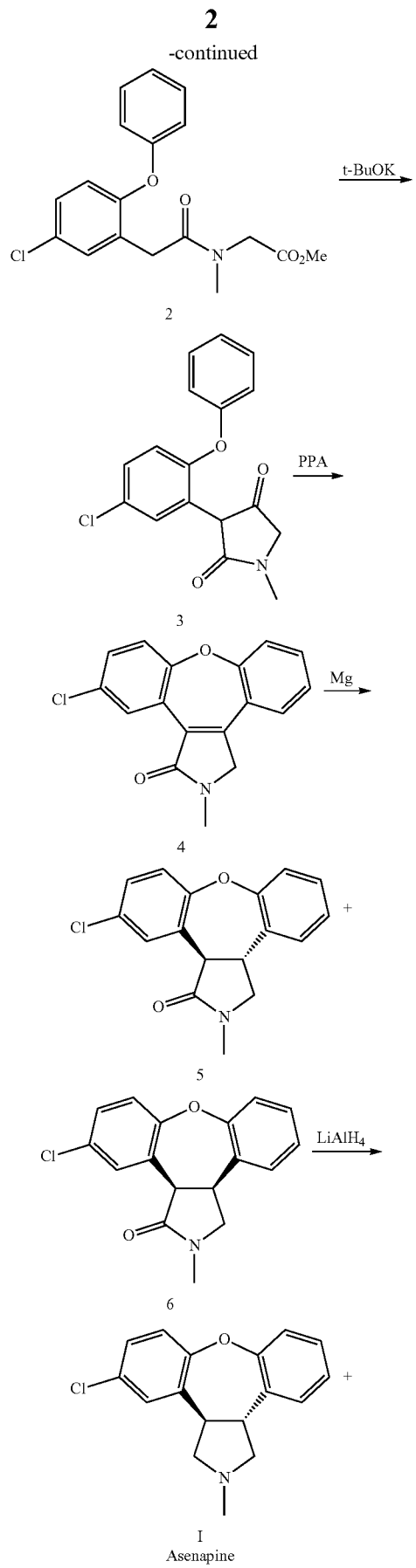

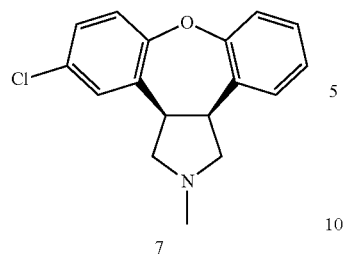

7

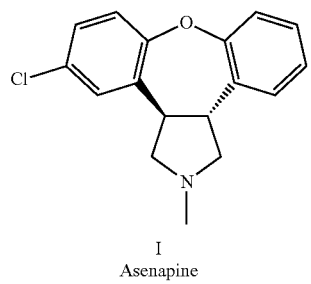

I
Asenapine

The main problem of this synthetic route is that the obtained Asenapine is a mixture of cis- and trans-isomers, the separation operations of the isomers are very complicated, and the yield is low, so this method is difficult to be used in industrial production.

The literature in 2008 (*Org. Process Res. Dev.,* 2008, 12 (2), 196-201) reported an improvement of the above synthetic method. Its method is as follows:

This method is characterized in that a strong base is used to hydrolyze and open the lactam ring and the isomerization reaction occurs at the same time, and then the ring is closed to obtain the desired trans lactam intermediate, which is finally reduced to Asenapine with lithium aluminum hydride. This modification solves the problem in product separation and purification, and improves the overall yield. However, this synthetic route is long, and the starting material 2-(5-chloro-2-phenoxy)phenylacetic acid has to be synthesized by the following method. In addition, the above method contains multiple reaction steps using reagents that are harmful to the environment and dangerous reagents such as lithium aluminum hydride, etc., thus the method is not conducive to industrial production.

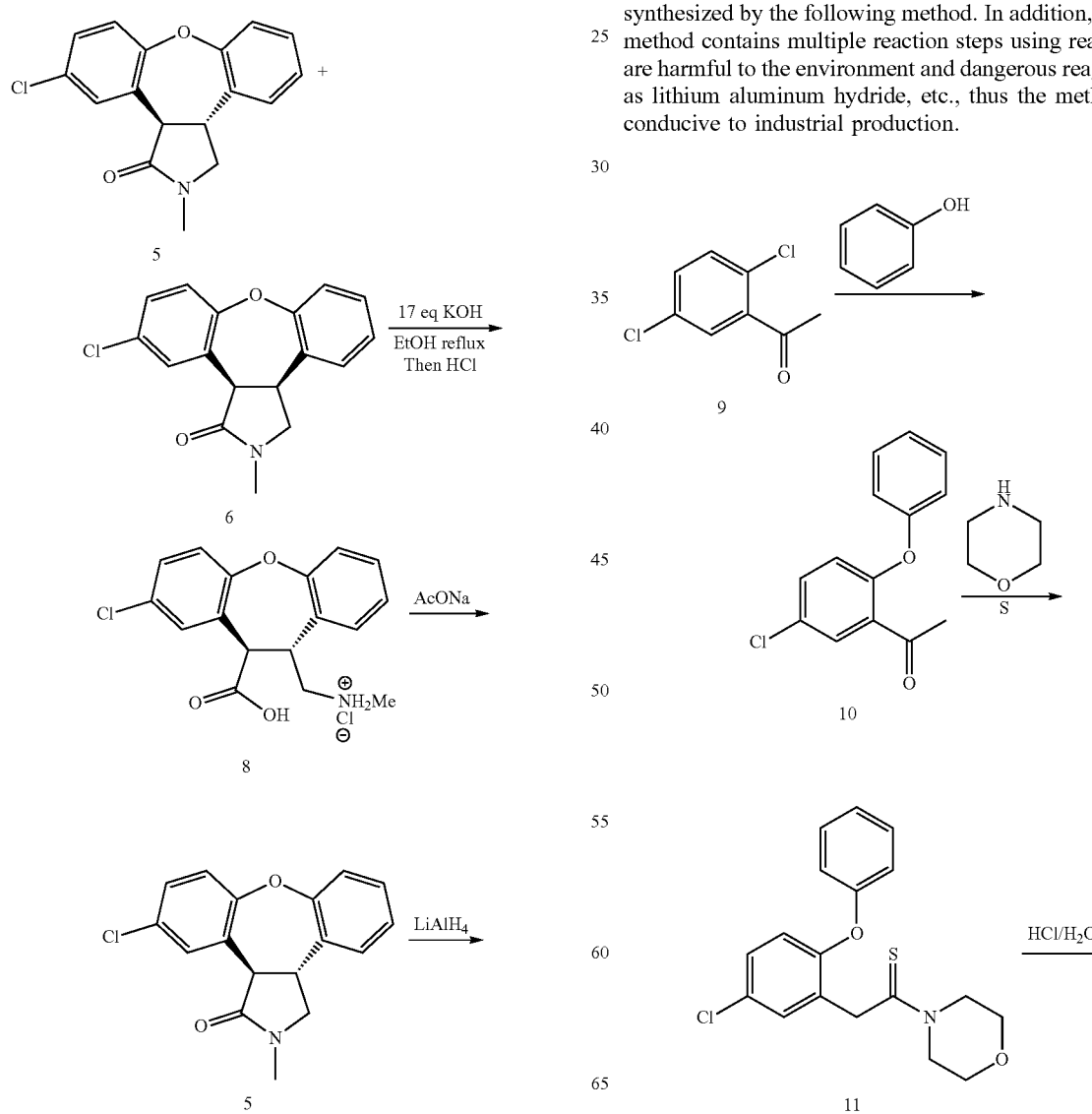

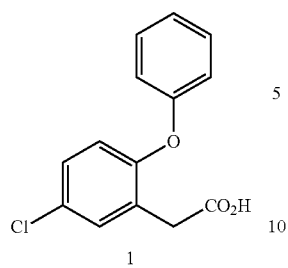

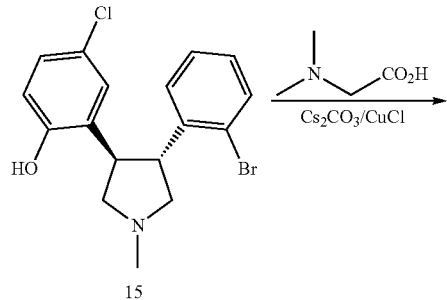

Afterwards, the patent US2008009619 in 2008 reported that o-bromobenzyl bromide is used as raw material to react with triethyl phosphite to obtain benzyl phosphonate, which is then reacted with salicylaldehyde through Horner-Wadsworth-Emmons reaction to obtain trans tetrahydropyrrole intermediate, which is finally subjected to the intramolecular Ullmann reaction to obtain the desired compound.

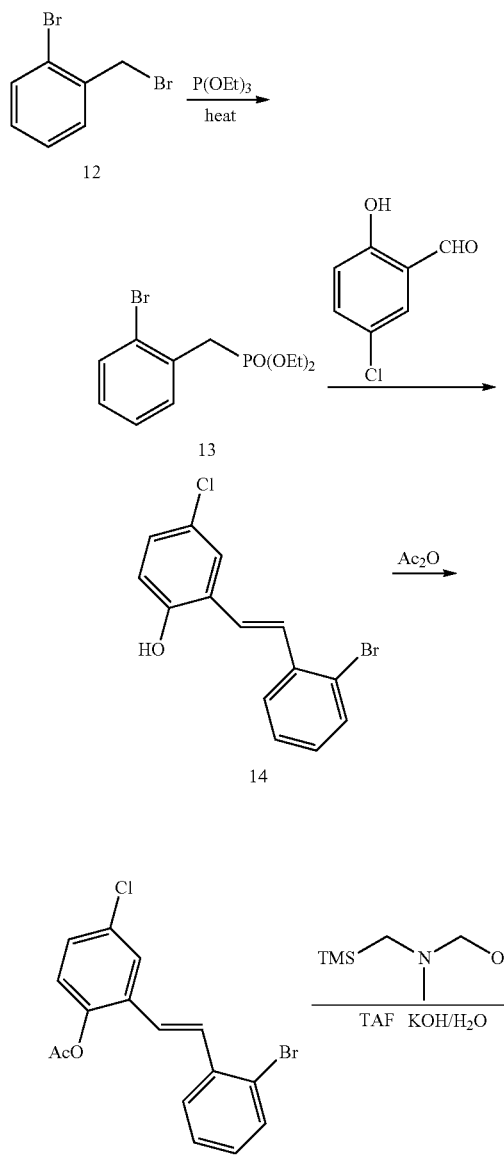

Although this method has a short synthetic route and a single isomer is obtained, the preparation of benzyl phosphonate requires the use of o-bromobenzyl bromide which is a highly stimulatory raw material, and requires a long-time high-temperature reaction. Moreover, the Ullmann reaction in the final step has low yield, and requires long-time high-temperature reaction in the presence of cesium carbonate, cuprous halide and N, N-dimethylglycine, thereby resulting in not only environmental pollution problems, but also high production costs.

Similar to the above synthetic method, a new technology for synthesis of Asenapine was reported by CN102229613 in 2011:

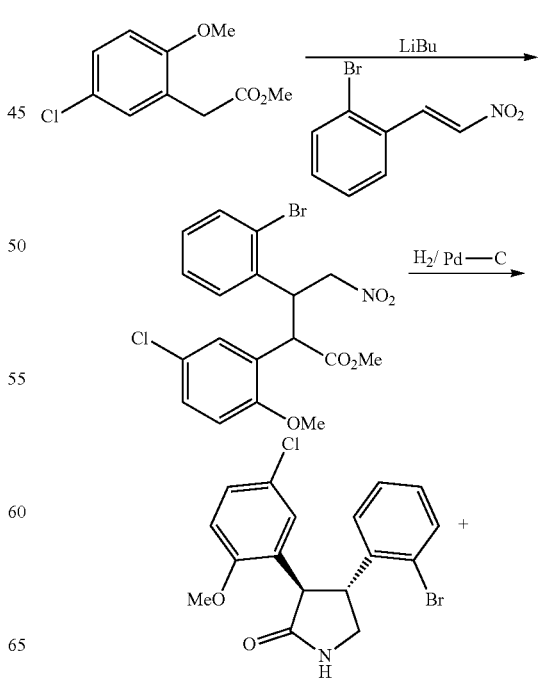

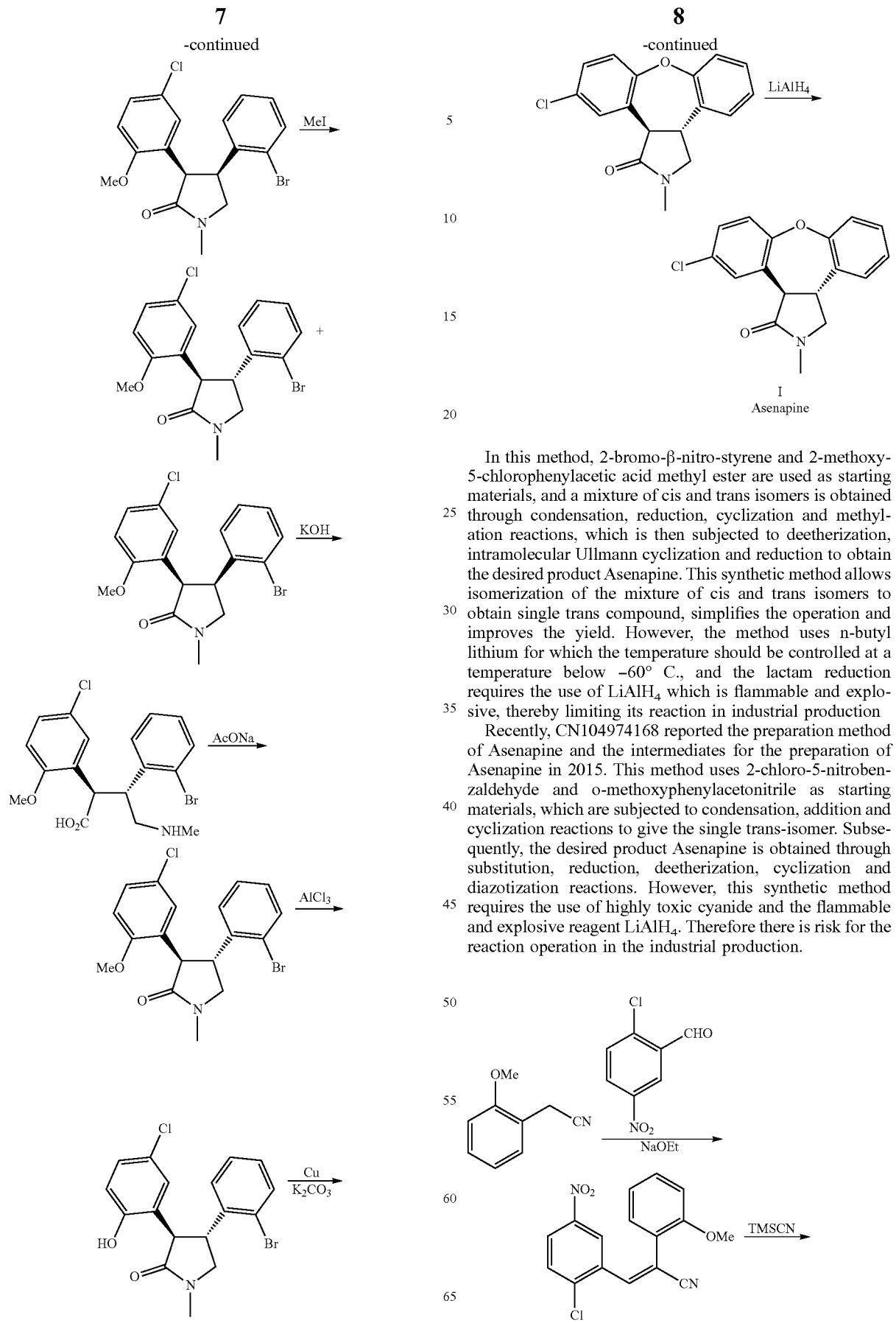

In this method, 2-bromo-β-nitro-styrene and 2-methoxy-5-chlorophenylacetic acid methyl ester are used as starting materials, and a mixture of cis and trans isomers is obtained through condensation, reduction, cyclization and methylation reactions, which is then subjected to deetherization, intramolecular Ullmann cyclization and reduction to obtain the desired product Asenapine. This synthetic method allows isomerization of the mixture of cis and trans isomers to obtain single trans compound, simplifies the operation and improves the yield. However, the method uses n-butyl lithium for which the temperature should be controlled at a temperature below −60° C., and the lactam reduction requires the use of LiAlH$_4$ which is flammable and explosive, thereby limiting its reaction in industrial production Recently, CN104974168 reported the preparation method of Asenapine and the intermediates for the preparation of Asenapine in 2015. This method uses 2-chloro-5-nitrobenzaldehyde and o-methoxyphenylacetonitrile as starting materials, which are subjected to condensation, addition and cyclization reactions to give the single trans-isomer. Subsequently, the desired product Asenapine is obtained through substitution, reduction, deetherization, cyclization and diazotization reactions. However, this synthetic method requires the use of highly toxic cyanide and the flammable and explosive reagent LiAlH$_4$. Therefore there is risk for the reaction operation in the industrial production.

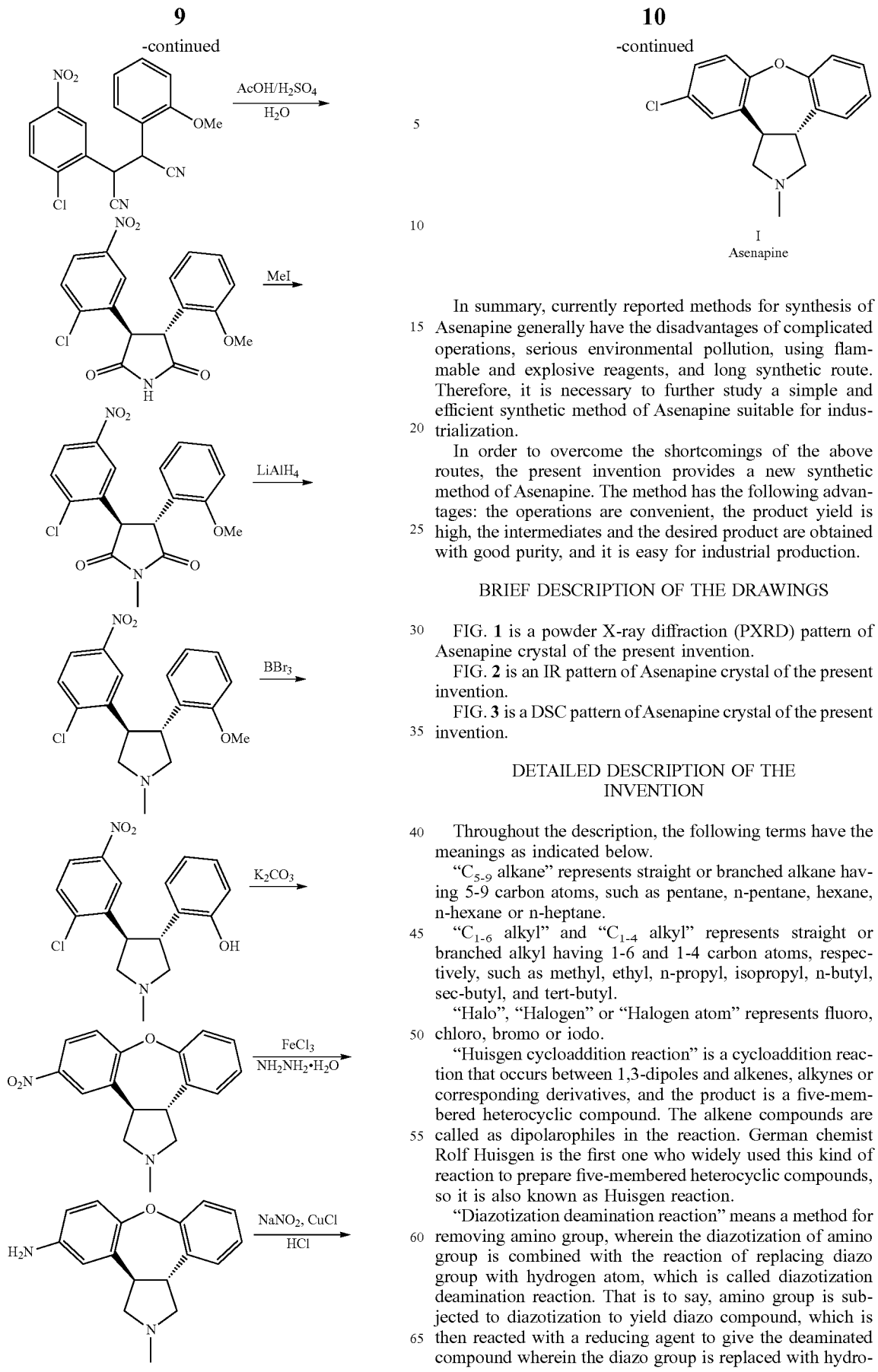

Asenapine

In summary, currently reported methods for synthesis of Asenapine generally have the disadvantages of complicated operations, serious environmental pollution, using flammable and explosive reagents, and long synthetic route. Therefore, it is necessary to further study a simple and efficient synthetic method of Asenapine suitable for industrialization.

In order to overcome the shortcomings of the above routes, the present invention provides a new synthetic method of Asenapine. The method has the following advantages: the operations are convenient, the product yield is high, the intermediates and the desired product are obtained with good purity, and it is easy for industrial production.

DETAILED DESCRIPTION OF THE INVENTION

Figure 1:
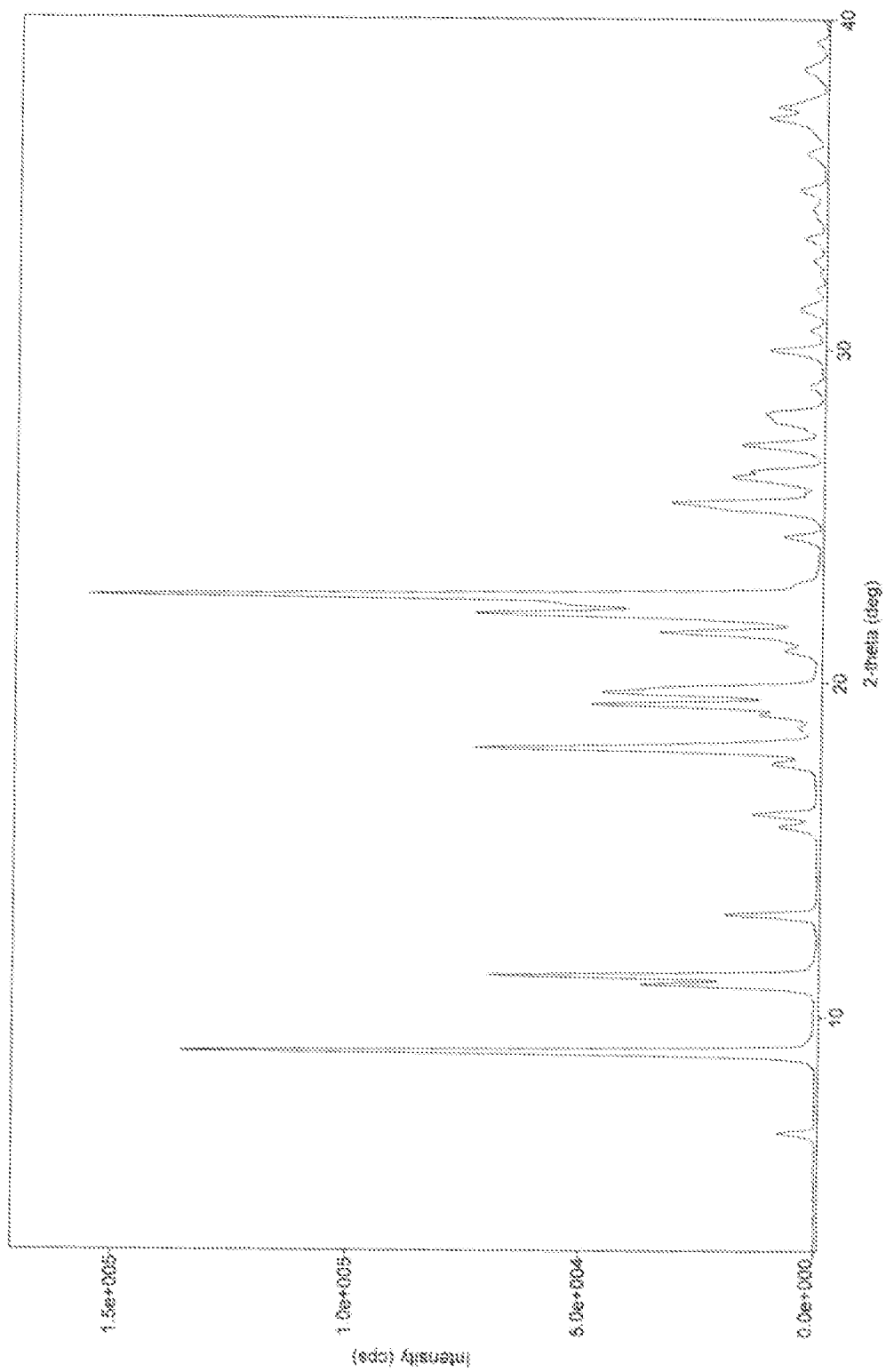
FIG. 1 is a powder X-ray diffraction (PXRD) pattern of Asenapine crystal of the present invention.

Throughout the description, the following terms have the meanings as indicated below.

"$C_{5-9}$ alkane" represents straight or branched alkane having 5-9 carbon atoms, such as pentane, n-pentane, hexane, n-hexane or n-heptane.

"$C_{1-6}$ alkyl" and "$C_{1-4}$ alkyl" represents straight or branched alkyl having 1-6 and 1-4 carbon atoms, respectively, such as methyl, ethyl, n-propyl, isopropyl, n-butyl, sec-butyl, and tert-butyl.

"Halo", "Halogen" or "Halogen atom" represents fluoro, chloro, bromo or iodo.

"Huisgen cycloaddition reaction" is a cycloaddition reaction that occurs between 1,3-dipoles and alkenes, alkynes or corresponding derivatives, and the product is a five-membered heterocyclic compound. The alkene compounds are called as dipolarophiles in the reaction. German chemist Rolf Huisgen is the first one who widely used this kind of reaction to prepare five-membered heterocyclic compounds, so it is also known as Huisgen reaction.

"Diazotization deamination reaction" means a method for removing amino group, wherein the diazotization of amino group is combined with the reaction of replacing diazo group with hydrogen atom, which is called diazotization deamination reaction. That is to say, amino group is subjected to diazotization to yield diazo compound, which is then reacted with a reducing agent to give the deaminated compound wherein the diazo group is replaced with hydrogen atom.

The objective of the present invention is to provide a new method of preparing Asenapine and a new crystal form of Asenapine free base is obtained.

In a first aspect, the present invention provides a method for preparing Asenapine of formula I:

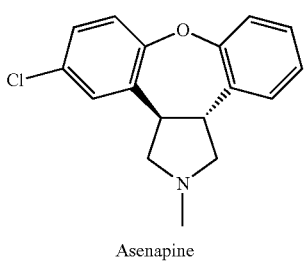

Asenapine the method comprising the following steps:

(a-1) Intermediate II is subjected to internal nucleophilic substitution under basic condition to give cyclic ether Intermediate III,

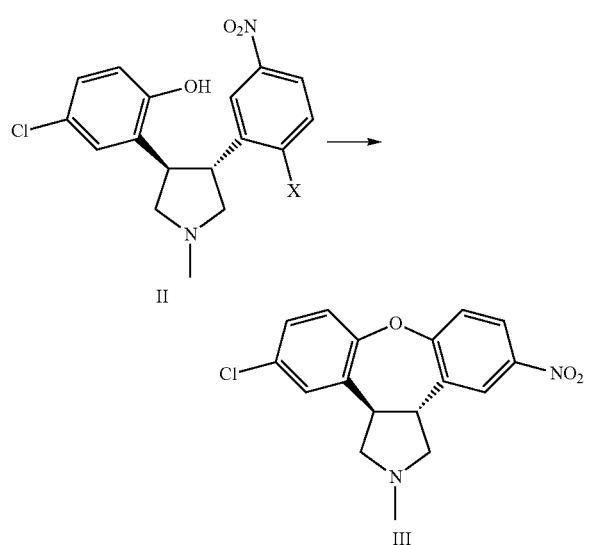

wherein X is F, Cl, Br or I, wherein the base is alkali metal hydroxide, alkali metal carbonate, alkali metal bicarbonate, metal hydride, organometallic compounds or non-nucleophilic organic strong base, (a-2) the nitro group of intermediate III is reduced to obtain intermediate IV,

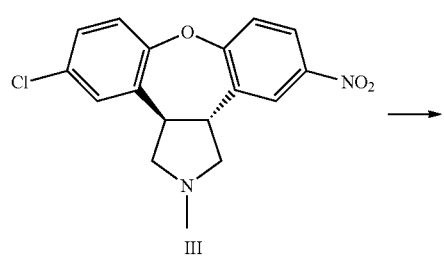

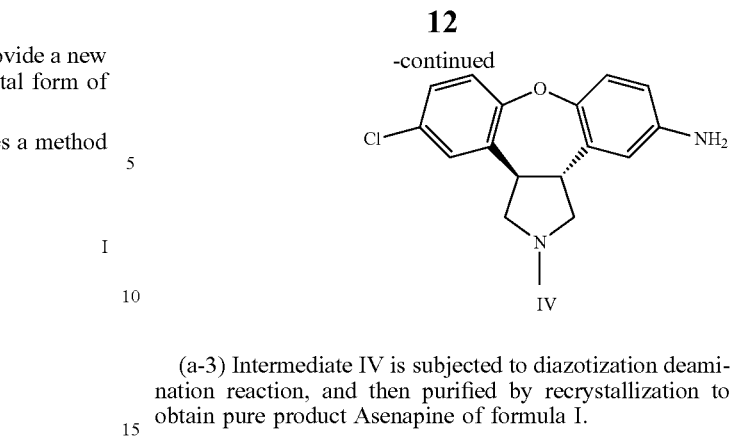

(a-3) Intermediate IV is subjected to diazotization deamination reaction, and then purified by recrystallization to obtain pure product Asenapine of formula I.

In said step (a-1), the halogen-substituted benzene ring of the intermediate II is reacted with the phenolic hydroxyl group on another benzene ring under basic and mild condition in aprotic solvent to perform internal nucleophilic substitution to yield the cyclic ether intermediate III.

The base used in this step is selected from alkali metal hydroxides LiOH, NaOH, KOH, RbOH, CsOH, FrOH; alkali metal carbonates $Li_2CO_3$, $Na_2CO_3$, $K_2CO_3$, $Rb_2CO_3$, $Cs_2CO_3$; alkali metal bicarbonates $NaHCO_3$, $KHCO_3$; organometallic compounds butyl lithium, methyl magnesium chloride, tert-butyl magnesium chloride, ethyl magnesium bromide, butyl magnesium bromide; metal hydrides NaH, KH, $CaH_2$; and non-nucleophilic organic strong base LDA, LiHMDS or NaHMDS.

The solvent in the reaction is aprotic solvent, for example, selected from toluene, xylene, tetrahydrofuran, methyltetrahydrofuran, diethyl ether, isopropyl ether, methyl tert-butyl ether, dioxane, acetonitrile, sulfolane, N-methylpyrrolidone, DMF, DMSO, glycol dimethyl ether, diethylene glycol dimethyl ether, or a mixture of two or more thereof.

The reaction temperature is 0 to 100° C., preferably 20 to 70° C.

After the reaction is completed, the mixture is cooled to room temperature, to which drinking water is added to precipitate the product. The resulting product is filtered, and dried under vacuum to constant weight to obtain cyclic ether intermediate III.

In said step (a-2), the nitro group of intermediate III is reduced by catalytic hydrogenation to obtain intermediate IV.

The solvent used in this step is $C_{1-4}$ alcohol solvent, for example, methanol, ethanol, propanol, isopropanol, butanol, isobutanol, tert-butanol or water, or a mixture of two or more thereof.

The reaction temperature is 30 to 70° C.

In this reaction, the nitro group is reduced by catalytic hydrogenation to amino group, in which the reducing agent used can be selected from Pd/C, Ni, iron, zinc, or sodium sulfide.

In said step (a-3), intermediate IV is subjected to diazotization deamination reaction, and then purified by recrystallization to obtain pure product Asenapine of formula I.

Intermediate IV is dissolved in the reducing agent of the diazotization deamination reaction, to which is added the diazotization reagent dropwise at −5 to 30° C. The reaction is carried out in one-pot manner. The pH value is adjusted to neutral pH with base, then a solid precipitates and is filtered to obtain the crude product, which is then subjected to recrystallization to obtain Asenapine in crystalline form.

The diazotization reagent used in this reaction is nitrite, such as sodium nitrite or potassium nitrite.

The reducing agent used for the diazotization deamination reaction in this reaction can be selected from methanol, ethanol, isopropanol, hypophosphorous acid, borohydride (including sodium borohydride, potassium borohydride) or nitrite.

The nitrite is selected from methyl nitrite, ethyl nitrite, tert-butyl nitrite, n-pentyl nitrite or isoamyl nitrite.

The base used in this step can be selected from sodium hydroxide, potassium hydroxide, sodium carbonate, sodium bicarbonate, potassium carbonate, potassium bicarbonate, aqueous ammonia, aqueous methylamine solution, or triethylamine.

The solvent used in the purification by recrystallization is selected from $C_{5-9}$ alkanes (e.g. n-pentane, hexane, n-hexane or n-heptane or a mixture of two or more thereof), aromatic hydrocarbon solvents (e.g. benzene, toluene, xylene, chlorobenzene, or a mixture of two or more thereof), ester solvents (e.g. ethyl formate, methyl acetate, ethyl acetate, propyl acetate, isopropyl acetate, butyl acetate, tert-butyl acetate, or a mixture of two or more thereof), ketone solvents (e.g. acetone, butanone or their mixture), ether solvents (e.g. diethyl ether, isopropyl ether, methyl tertbutyl ether, tetrahydrofuran, methyltetrahydrofuran, or a mixture of two or more thereof), alcohol solvents (e.g. methanol, ethanol, propanol, isopropanol, or a mixture of two or more thereof), water, or a mixture of two or more of the above solvents, preferably n-heptane or a mixture thereof with other solvents.

In a second aspect, a method for preparing Asenapine of formula I, comprising the following steps:

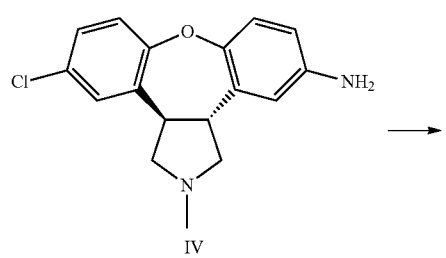

IV

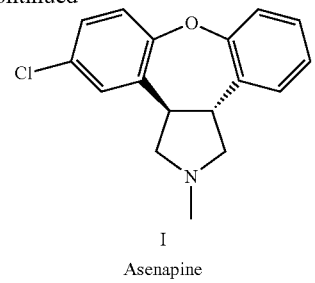

Asenapine wherein intermediate IV is subjected to diazotization deamination reaction, and then purified by recrystallization to obtain Asenapine of formula I.

Intermediate IV is dissolved in the reducing agent used in the diazotization deamination reaction, to which is added the diazotization reagent dropwise at −5 to 30° C. The reaction is carried out in one-pot manner. The pH value is adjusted to neutral pH with base, then a solid precipitates and is filtered to obtain the crude product, which is then subjected to recrystallization to obtain Asenapine in crystalline form.

The diazotization reagent used in this reaction is sodium nitrite or potassium nitrite.

The reducing agent used in this reaction can be selected from methanol, ethanol, isopropanol, hypophosphorous acid, borohydride (including sodium borohydride, potassium borohydride) or nitrite.

The nitrite is selected from methyl nitrite, ethyl nitrite, tert-butyl nitrite, n-pentyl nitrite or isoamyl nitrite.

In a third aspect, the present invention provides a crystal of Asenapine of formula I, and a method for preparing the crystal.

The present invention provides a crystal form of Asenapine of formula I, characterized in that when powder X-ray diffraction analysis is carried out under the experimental condition of CuKα radiation, the characteristic diffraction positions expressed in 2-theta angle (2θ) are 9.0±0.2°, 11.2±0.2°, 18.0±0.2°, 22.1±0.2°, 22.4±0.2°, 22.6±0.2°.

More particularly, in the PXRD pattern of crystal of Asenapine of formula I, the characteristic diffraction positions expressed in 2-theta angle (2θ) are 9.0±0.2°, 10.9±0.2°, 11.2±0.2°, 18.0±0.2°, 19.4±0.2°, 19.7±0.2°, 21.5±0.2, 22.1±0.2°, 22.4±0.2°, 22.6±0.2°, 25.3±0.2°.

Figure 2:
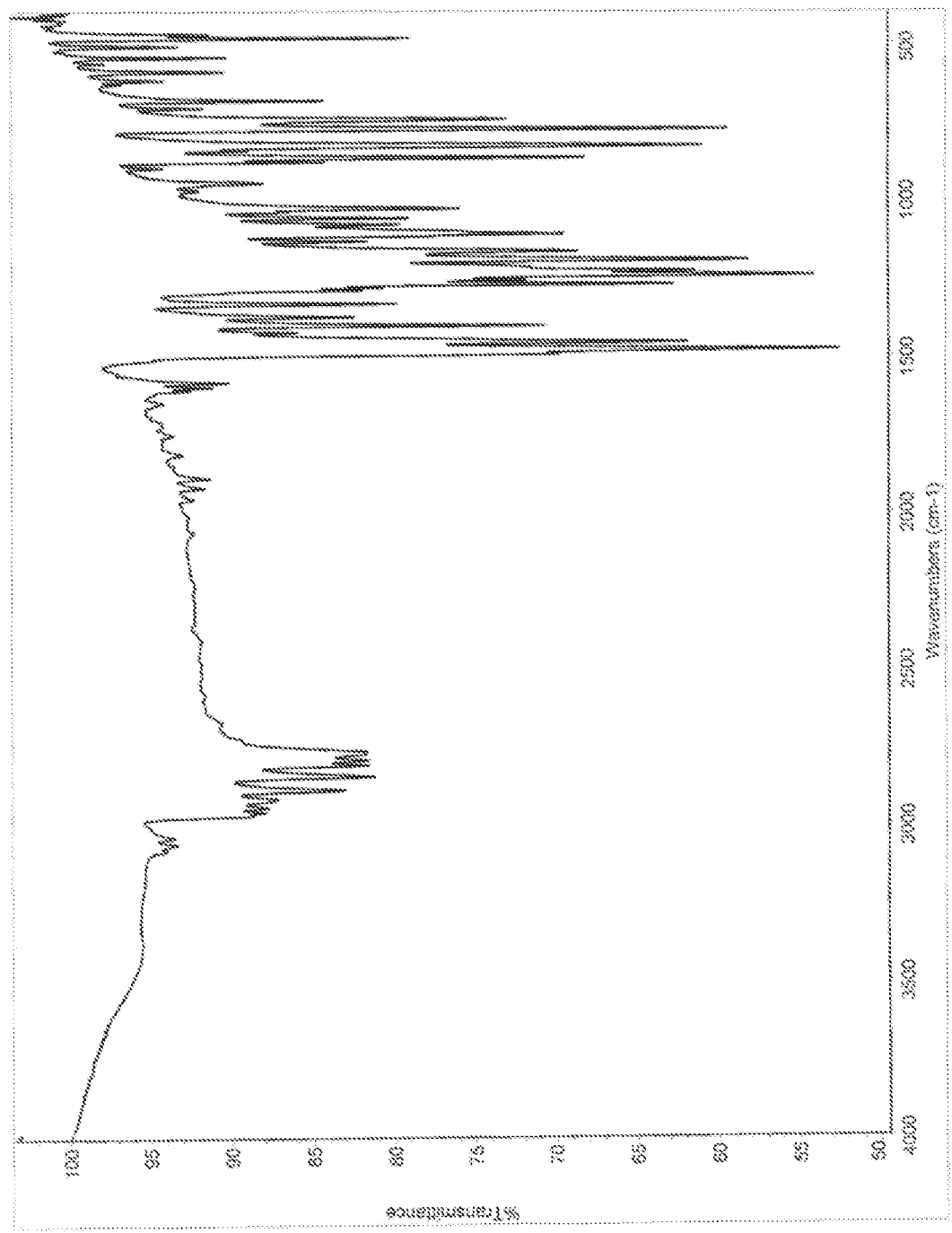
FIG. 2 is an IR pattern of Asenapine crystal of the present invention.
Figure 3:
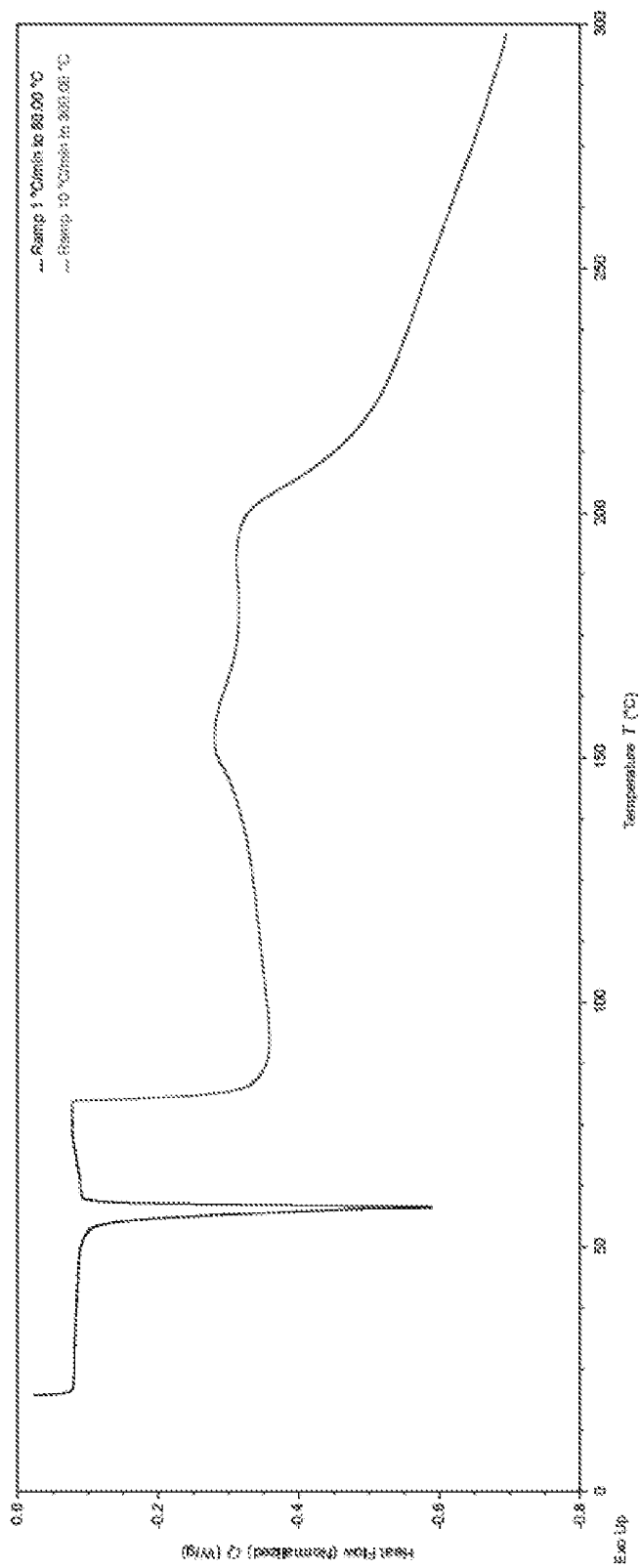
FIG. 3 is a DSC pattern of Asenapine crystal of the present invention.

The PXRD pattern of crystal of Asenapine of formula I is shown in FIG. 1, the IR pattern thereof is shown in FIG. 2, and the DSC pattern thereof is shown in FIG. 3.

The preparation method and purification method of the present invention is used to obtain a crystal form of Asenapine of formula I, which is characterized in that, when powder X-ray diffraction analysis is carried out under the experimental condition of CuKα radiation, the diffraction positions 2θ angles (°) or d values (Å), and peak height values (Height %) or peak area values (Area %) representing relative intensity of diffraction peaks are shown as below:

| Ser. No. | Angle [2θ] | d value [Angstrom] | Relative intensity [%] |
|---|---|---|---|
| 1 | 6.52 | 13.546 | 4 |
| 2 | 8.97 | 9.847 | 72 |
| 3 | 10.97 | 8.056 | 20 |
| 4 | 11.24 | 7.866 | 39 |
| 5 | 13.07 | 6.767 | 11 |
| 6 | 15.69 | 5.643 | 5 |
| 7 | 16.06 | 5.513 | 8 |

-continued

| Ser. No. | Angle [2θ] | d value [Angstorm] | Relative intensity [%] |
|---|---|---|---|
| 8 | 17.55 | 5.050 | 6 |
| 9 | 18.02 | 4.920 | 56 |
| 10 | 18.62 | 4.761 | 1 |
| 11 | 19.02 | 4.662 | 7 |
| 12 | 19.35 | 4.585 | 27 |
| 13 | 19.70 | 4.502 | 30 |
| 14 | 19.85 | 4.469 | 12 |
| 15 | 20.96 | 4.234 | 8 |
| 16 | 21.53 | 4.123 | 24 |
| 17 | 22.10 | 4.020 | 51 |
| 18 | 22.35 | 3.975 | 42 |
| 19 | 22.62 | 3.928 | 100 |
| 20 | 24.39 | 3.647 | 4 |
| 21 | 25.28 | 3.520 | 25 |
| 22 | 25.42 | 3.501 | 9 |
| 23 | 26.18 | 3.401 | 10 |
| 24 | 26.38 | 3.376 | 12 |
| 25 | 27.13 | 3.328 | 14 |
| 26 | 27.91 | 3.194 | 14 |
| 27 | 28.12 | 3.171 | 5 |
| 28 | 28.87 | 3.091 | 2 |
| 29 | 30.00 | 2.976 | 8 |
| 30 | 30.60 | 2.920 | 2 |
| 31 | 31.24 | 2.861 | 5 |
| 32 | 31.86 | 2.807 | 1 |
| 33 | 32.72 | 2.735 | 1 |
| 34 | 33.38 | 2.682 | 2 |
| 35 | 34.82 | 2.574 | 3 |
| 36 | 35.95 | 2.496 | 2 |
| 37 | 37.03 | 2.426 | 11 |
| 38 | 37.31 | 2.408 | 9 |
| 39 | 38.47 | 2.338 | 4 |
| 40 | 39.29 | 2.291 | 1 |

The method for preparing the crystal form of Asenapine having formula I comprises: dissolving the crude product of Asenapine in the recrystallization solvent, crystallizing with stirring at room temperature, filtering, and drying under vacuum to obtain Asenapine free base in said crystal form.

The solvent used in the purification by recrystallization can be selected from $C_{1-9}$ alkanes (e.g. n-pentane, hexane, n-hexane or n-heptane or a mixture of two or more thereof), aromatic hydrocarbon solvents (e.g. benzene, toluene, xylene, chlorobenzene, or a mixture of two or more thereof), ester solvents (e.g. ethyl formate, methyl acetate, ethyl acetate, propyl acetate, isopropyl acetate, butyl acetate, tert-butyl acetate, or a mixture of two or more thereof), ketone solvents (e.g. acetone, butanone or their mixture), ether solvents (e.g. diethyl ether, isopropyl ether, methyl tert-butyl ether, tetrahydrofuran, methyltetrahydrofuran, or a mixture of two or more thereof), alcohol solvents (e.g. methanol, ethanol, propanol, isopropanol, or a mixture of two or more thereof), water, or a mixture of two or more of above solvents, preferably n-heptane or a mixture thereof with other solvents.

In an embodiment, the method for preparing the crystal form of Asenapine of formula I comprises: The recrystallization solvent, such as hexane, n-hexane or n-heptane, or a mixture thereof with toluene, xylene, ethyl acetate, isopropyl acetate, isopropyl ether, tetrahydrofuran or methyltetrahydrofuran, is added to the crude Asenapine. After the crude product is dissolved with heating and stirring, a solid is precipitated by cooling, which is collected by filtration and dried in vacuo to obtain the crystalline compound of formula I.

The temperature for dissolving is 30 to 70° C., preferably 35 to 50° C.

The temperature for precipitating the crystal is 15 to 25° C. After the temperature of 15 to 25° C. is maintained to precipitate the crystal for 1.0 to 1.5 h, the temperature is reduced to −20 to 0° C., preferably −20 to −10° C., in a rate of 5-10° C./hour. After the mixture is maintained at the temperature with stirring for 1.0 to 1.5 h, the mixture is filtered, and washed with appropriate amount of hexane, n-hexane or n-heptane. The resulting product is filtered and subjected to vacuum drying at 30 to 60° C., to yield the crystalline compound of formula I.

In another embodiment, the method for preparing the crystal form of Asenapine of formula I comprises: The recrystallization solvent, such as acetone, methanol, ethanol, propanol or isopropanol, is added to the crude Asenapine. After it is dissolved with heating, water is added and a solid is precipitated by cooling. Alternatively, a mixture of acetone, methanol, ethanol, propanol or isopropanol with water is added to the crude Asenapine. After it is dissolved with heating, a solid is precipitated by cooling. The resulting solid is collected by filtration, and dried in vacuo to obtain the crystalline compound of formula I.

The temperature for dissolving is 30 to 70° C., preferably 35 to 50° C.

The temperature for precipitating the crystal is 20 to 25° C. After the temperature of 20 to 25° C. is maintained to precipitate the crystal for 1.0 to 1.5 h, the temperature is reduced to −5 to 15° C., preferably −5 to 5° C., in a rate of 5-10° C./hour. After the mixture is maintained at the temperature with stirring for 1.0 to 1.5 h, the mixture is filtered, and washed with appropriate amount of the crystallization solvent. The resulting product is filtered and subjected to vacuum drying at 30 to 60° C., to yield the crystalline compound of formula I.

The method for preparing the crystal of Asenapine of formula I can further comprise: Asenapine acid salt is dissolved with water or organic solvent, and is neutralized with corresponding equivalents of base. The resulting solution is extracted with aprotic solvent and concentrated to dryness, and then the crystal is prepared according to the recrystallization methods described above.

The organic solvent used for dissolving can be selected from methanol, ethanol, isopropanol, N-methylpyrrolidone, DMF, DMSO, acetonitrile, tetrahydrofuran or methyltetrahydrofuran.

Asenapine acid salt may be selected from hydrochloride, hydrobromate, hydroiodide, maleate, fumarate or tartrate.

The base can be selected from sodium bicarbonate, sodium carbonate, potassium bicarbonate, potassium carbonate, cesium carbonate, lithium hydroxide, sodium hydroxide, potassium hydroxide, sodium tert-butoxide or potassium tert-butoxide.

The aprotic organic solvent can be selected from hexane, n-hexane, n-heptane, toluene, xylene, isopropyl ether, methyl tert-butyl ether, or a mixture of two or more thereof.

The obtained Asenapine of formula I can further form salt with an acid to prepare pharmaceutically acceptable salts thereof. This includes the reaction of Asenapine with hydrochloric acid to form salt to prepare Asenapine hydrochloride, or the reaction of Asenapine with maleic acid to form salt to prepare Asenapine maleate.

In a fourth aspect, the present invention provides the compound of formula II with the structure as below:

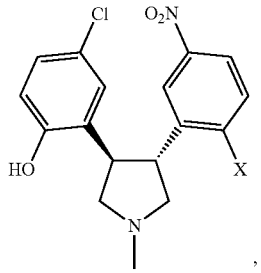
II wherein X is F, Cl, Br or I.

Specifically, the compound of formula II includes the following four compounds:

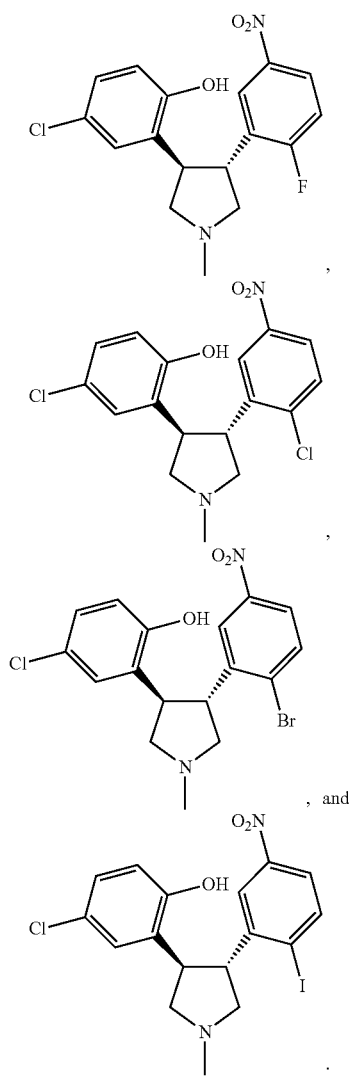
, and

Moreover, the present invention provides a method for preparing the compound of formula II, comprising the following steps:

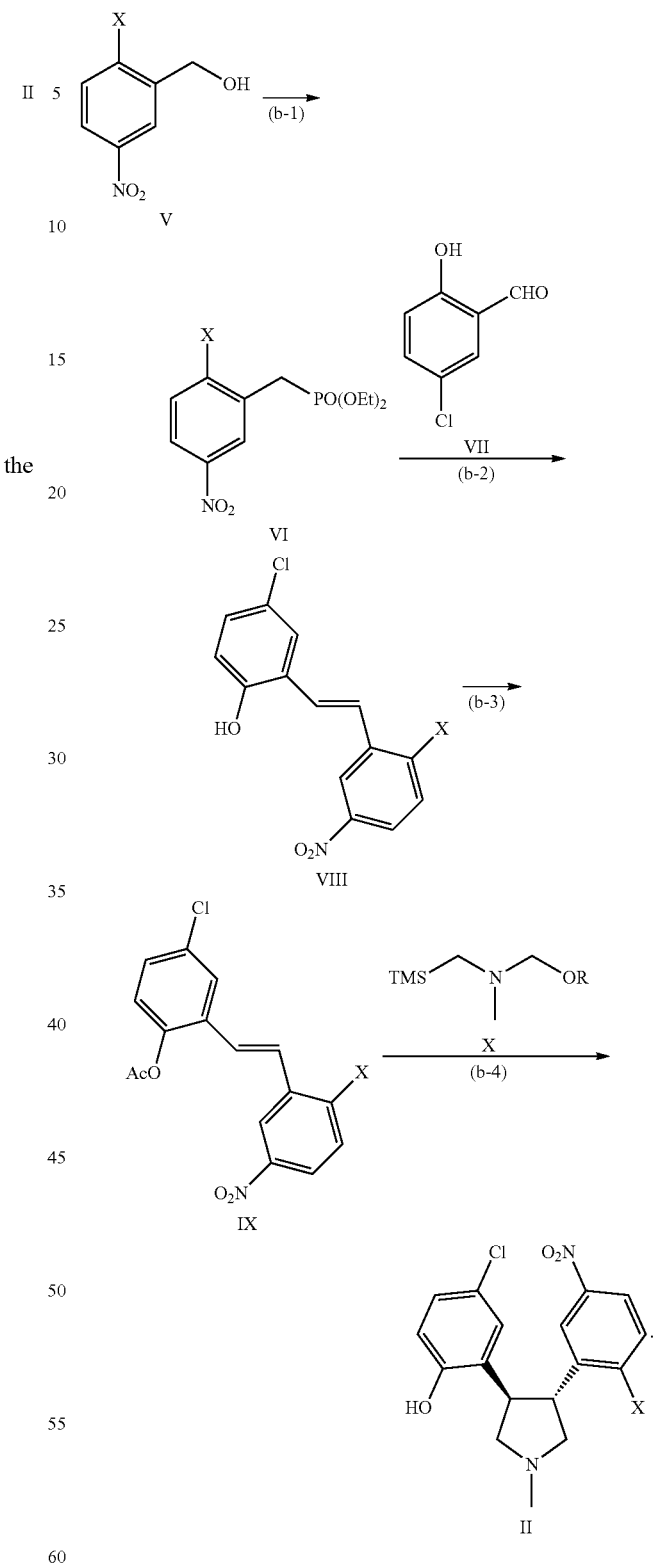

In said step (b-1), 2-halo-5-nitrophenylmethanol (V) is subjected to the action of sulfuric acid and hydrohalogen acid, thereby replacing the hydroxy group in its structure with a halogen atom, and then is reacted with triethyl phosphite under the catalysis of Lewis acid in an aprotic organic solvent to yield Intermediate VI.

The hydrohalogen acid used in this step includes hydrofluoric acid, hydrochloric acid, hydrobromic acid or hydroiodic acid. The Lewis acid is $FeCl_2$, $FeCl_3$, $FeBr_3$, $ZnCl_2$, $ZnBr_2$ or $InBr_2$.

The aprotic organic solvent can be selected from dichloromethane, chloroform, tetrahydrofuran, methyltetrahydrofuran, benzene, toluene, xylene, chlorobenzene, and the like, or a mixture of two or more thereof.

Specifically, Compound V (2-halo-5-nitro-phenylmethanol) and hydrohalogen acid and sulfuric acid are mixed at a weight ratio of 1.0:1.2 to 3.0:0.2 to 1.0 equivalent, and heated to 20 to 55° C. The reaction mixture is maintained at the temperature with stirring for 5 to 14 h, then is extracted with aprotic solvent, washed with drinking water and weak base, and dried with drying agent to remove water to obtain the intermediate solution. Then the catalyst Lewis acid and triethyl phosphite are added, and the reaction solution is heated to 30 to 50° C. and stirred for 6 to 12 h. After the reaction is completed, the mixture is cooled slightly, washed with drinking water, and the solution is partitioned into different layers. The organic layer is concentrated to dryness under reduced pressure to obtain the compound of formula VI, which is directly used in the next reaction step without purification.

The weight ratio of Compound V, hydrohalogen acid and sulfuric acid is preferably Compound V:halogen acid:sulfuric acid is 1.0:1.5 to 2.0:0.5 to 0.8. The reaction time is preferably 8 to 12 h.

The weak base mentioned above is selected from one or more of sodium carbonate, potassium carbonate, cesium carbonate, sodium bicarbonate or potassium bicarbonate. The drying agent is anhydrous magnesium sulfate or anhydrous sodium sulfate.

In said step (b-2), Intermediate VI is reacted with 5-chlorosalicylaldehyde VII under basic condition through Horner-Wadsworth-Emmons reaction to obtain intermediate VIII.

The molar ratio of intermediate VI and 5-chlorosalicylaldehyde in this step is intermediate VI:5-chlorosalicylaldehyde=1.0:1.2.

The base used can be selected from lithium hydroxide, sodium hydroxide, potassium hydroxide, lithium carbonate, sodium carbonate, potassium carbonate, sodium bicarbonate, potassium bicarbonate, potassium tert-butoxide, sodium tert-butoxide, or a mixture of two or more thereof.

The reaction solvent is aprotic solvent, which may be selected from benzene, toluene, xylene, chlorobenzene, tetrahydrofuran, methyltetrahydrofuran, isopropyl ether, methyl tert-butyl ether, or a mixture of two or more thereof.

The reaction temperature is −5 to 25° C., preferably −5 to 10° C.

In said step (b-3), Intermediate VIII is acetylated with acetic anhydride under basic condition to obtain intermediate IX.

The molar ratio of Intermediate VIII and acetic anhydride in this step is Intermediate VIII:acetic anhydride=1.0:1.8, preferably 1.2:1.5.

The base used may be selected from organic bases such as diethylamine, triethylamine, isopropylethylamine, pyridine or p-dimethylaminopyridine, or inorganic bases such as sodium carbonate, sodium bicarbonate, potassium carbonate, potassium bicarbonate, cesium carbonate, sodium hydride or potassium hydride.

The reaction solvent may be selected from benzene, toluene, xylene, chlorobenzene, tetrahydrofuran, methyltetrahydrofuran, isopropyl ether, methyl tert-butyl ether, or a mixture of two or more thereof.

The reaction temperature is 5 to 55° C.

For work-up, water, methanol, ethanol or isopropanol can be added to precipitate compound IX.

In said step (b-4), Intermediate IX is reacted with N-(alkoxymethyl)-N-methyl-(trimethylsilyl)methylamine in an aprotic solvent under the catalysis of trifluoroacetic acid at ambient temperature to perform Huisgen cycloaddition reaction, and then the deprotection is carried out under basic condition to obtain Intermediate II.

In the compound of formula X, R is $C_{1-6}$ alkyl, and R is preferably —$CH_3$和 -Bu-n.

The molar ratio of Intermediate IX and the compound of formula X in this step is Intermediate IX:Compound X=1.0: 1.5, preferably 1.1:1.3.

The reaction solvent in this step can be selected from benzene, toluene, xylene, chlorobenzene, tetrahydrofuran, methyltetrahydrofuran, isopropyl ether, methyl tert-butyl ether, or a mixture of two or more of said solvents.

The solvent used in deacetylation is $C_{1-4}$ alcohol solvent, selected from methanol, ethanol, propanol, isopropanol or butanol. The base used is alkali metal aqueous solution, which may be selected from lithium hydroxide, sodium hydroxide or potassium hydroxide aqueous solution.

In a fifth aspect, the present invention provides another method for preparing the compound of formula II:

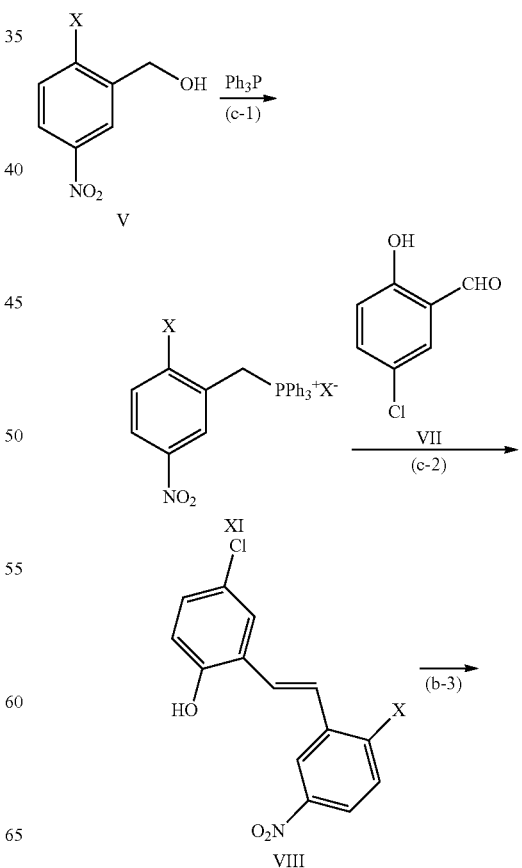

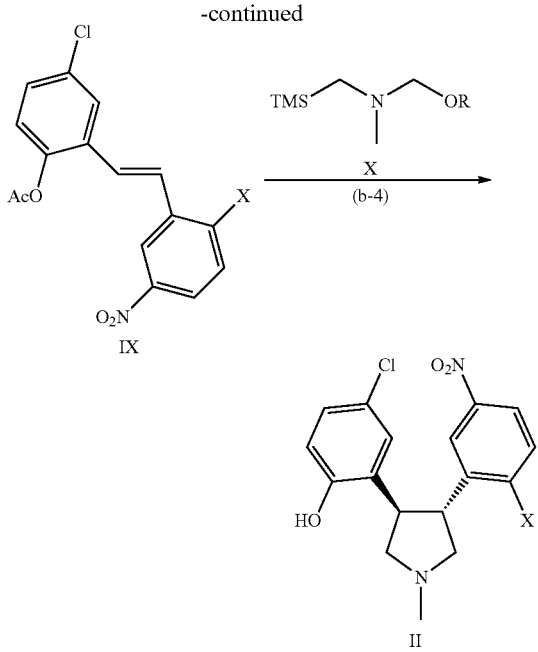

wherein X is F, Cl, Br or I.

In said step (c-1), Compound (V) is subjected to the action of sulfuric acid and hydrohalogen acid, thereby replacing the hydroxy group in its structure with a halogen atom, and then is reacted with triphenylphosphine in an aprotic organic solvent to obtain intermediate XI.

The hydrohalogen acid used in this step includes hydrofluoric acid, hydrochloric acid, hydrobromic acid or hydroiodic acid in various concentrations.

The aprotic organic solvent used can be selected from dichloromethane, chloroform, tetrahydrofuran, methyltetrahydrofuran, benzene, toluene, xylene, chlorobenzene, or a mixture of two or more thereof.

Specifically, Compound V (2-halo-5-nitro-phenylmethanol) and hydrohalogen acid and sulfuric acid are mixed at a weight ratio of 1.0:1.0 to 3.0:0.2 to 1.0 equivalent, and heated to 20 to 85° C. The reaction mixture is maintained at the temperature with stirring for 5 to 14 h, then is extracted with aprotic solvent, washed with drinking water and weak base, and dried with drying agent to remove water to obtain the intermediate solution. Then triphenylphosphine is added, and the reaction solution is heated to 30 to 70° C. and stirred for 6 to 12 h. After the reaction is completed, the mixture is cooled to room temperature, and filtered to obtain the compound of formula XI.

The weight ratio of Compound V, hydrohalogen acid and sulfuric acid is preferably Compound V:halogen acid:sulfuric acid is 1.0:1.2 to 1.5:0.2 to 0.5. The reaction time is preferably 8 to 12 h.

The weak base mentioned above is one or more of sodium carbonate, potassium carbonate, cesium carbonate, sodium bicarbonate or potassium bicarbonate. The drying agent is anhydrous magnesium sulfate or anhydrous sodium sulfate.

In said step (c-2), Intermediate XI is reacted with 5-chlorosalicylaldehyde VII under basic condition through Witting reaction to yield Intermediate VIII.

The base used in this step may be selected from inorganic bases, such as lithium hydroxide, sodium hydroxide, potassium hydroxide, sodium carbonate, potassium carbonate, sodium tert-butoxide, or potassium tert-butoxide, or organic bases, such as triethylamine, pyridine, p-dimethylaminopyridine, or diisopropylethylamine.

In this step, the molar ratio of Intermediate XI and 5-chlorosalicylaldehyde is 1:1.05 to 1.5, preferably 1:1.05 to 1.3.

The reaction temperature is 20 to 80° C., preferably 40 to 70° C.

The reaction solvent is an aprotic organic solvent, which may be selected from dichloromethane, chloroform, tetrahydrofuran, methyltetrahydrofuran, benzene, toluene, xylene, chlorobenzene, or a mixture of two or more thereof.

In said step (b-3), Intermediate VIII is acetylated with acetic anhydride under basic condition to obtain intermediate IX.

The molar ratio of Intermediate VIII and acetic anhydride in this step is Intermediate VIII:acetic anhydride=1.0:1.8, preferably 1.2:1.5.

The base used may be selected from organic bases such as diethylamine, triethylamine, isopropylethylamine, pyridine or p-dimethylaminopyridine, or inorganic bases such as sodium carbonate, sodium bicarbonate, potassium carbonate, potassium bicarbonate, cesium carbonate, sodium hydride or potassium hydride The reaction solvent may be selected from benzene, toluene, xylene, chlorobenzene, tetrahydrofuran, methyltetrahydrofuran, isopropyl ether, methyl tert-butyl ether, or a mixture of two or more thereof.

The reaction temperature is 5 to 55° C.

For work-up, water, methanol, ethanol or isopropanol can be added to precipitate compound IX.

In said step (b-4), Intermediate IX is reacted with N-(alkoxymethyl)-N-methyl-(trimethylsilyl)methylamine in an aprotic solvent under the catalysis of trifluoroacetic acid at ambient temperature to perform Huisgen cycloaddition reaction, and then the deprotection is carried out under basic condition to obtain Intermediate II.

In the compound of formula X, R may be $C_{1-6}$ alkyl, and R is preferably —$CH_3$和 -Bu-n.

The molar ratio of Intermediate IX and the compound of formula X in this step is Intermediate IX:Compound X=1.0:1.5, preferably 1.1:1.3.

The reaction solvent in this step can be selected from benzene, toluene, xylene, chlorobenzene, tetrahydrofuran, methyltetrahydrofuran, isopropyl ether, methyl tert-butyl ether, or a mixture of two or more of said solvents.

The solvent used in deacetylation is $C_{1-4}$ alcohol solvent, selected from methanol, ethanol, propanol, isopropanol or butanol. The base used is alkali metal aqueous solution, which may be selected from lithium hydroxide, sodium hydroxide or potassium hydroxide aqueous solution.

The key points of the present invention include: using catalysis of Lewis acid, 2-halo-5-nitrobenzyl halide is reacted with triethyl phosphite under mild reaction condition to yield Intermediate IV, thereby avoiding the use of high-temperature and long-time reaction with 2-bromo-benzyl bromide to prepare the phosphonate described in the prior art (US2008009619). By use of the strong electrophilic effect of the nitro group at para-position of halogen atom on the tetrahydropyrrole-benzene ring of Intermediate II, the internal nucleophilic substitution occurs between the halogen atom and the phenolic hydroxyl group on another benzene ring under basic and mild condition, creating the dibenzo[2,3:6,7]oxepino[4,5-c]pyrrole ring, thus it overcomes the defect that the construction of dibenzo[2,3:6,7] oxepino[4,5-c]pyrrole ring of Asenapine described in the prior art (US2008009619) requires long-time and high-temperature Intramolecular Ullmann reaction. Further, the purification method of Asenapine is improved and a new crystal form of Asenapine free base is obtained. The crystallization method and the crystal obtained can simplify the work-up operations, improve the purification efficiency, and reduce the costs, thus are very advantageous for large-scale industrial production.

Compared with the prior art, the method of preparing Asenapine according to the present invention avoids using the dangerous, flammable and explosive reducing agent $LiAlH_4$ which was used in the prior art (U.S. Pat. No. 4,145,434, Org. Process Res. Dev., 2008, 12 (2), 196-201, CN102229613, and CN104974168), and avoids the process of separation and purification of isomers, thereby simplifying the procedure. Furthermore, the method of the present invention does not require high-temperature and long-time reaction operations (US2008009619), avoids using dangerous and highly toxic reagents butyl lithium and methyl iodide (CN102229613), and does not use methyl iodide, boron tribromide and hydrazine hydrate (CN104974168). The present invention has the advantages of mild reaction condition, simple operations, less environmental pollution, low costs, and the like, thus it is more suitable for the industrial production.

EXAMPLES

The method of the present invention will be further explained by the following examples. It should be understood that the following examples are provided to help better understand the present invention, not intended to limit the scope of the present invention in any manner.

Example 1

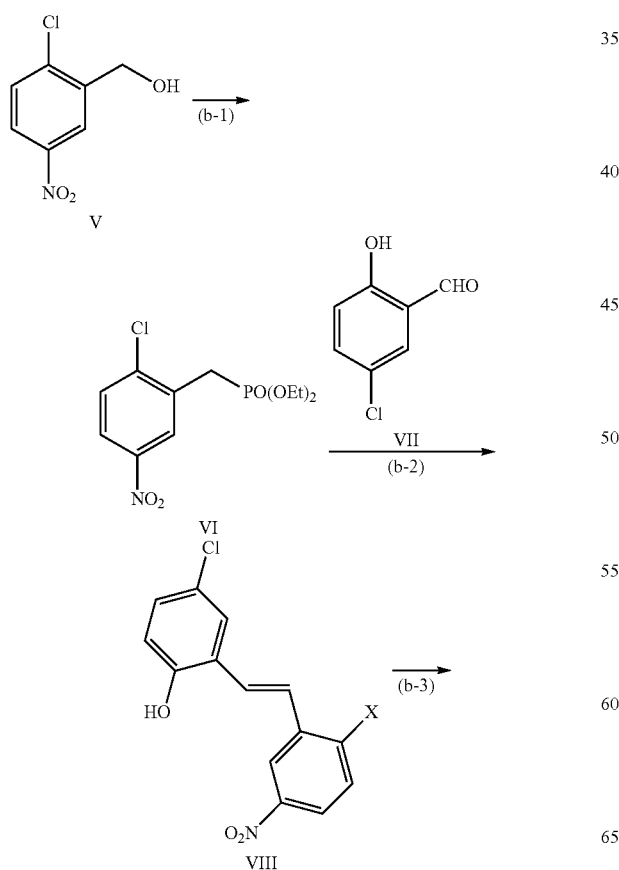

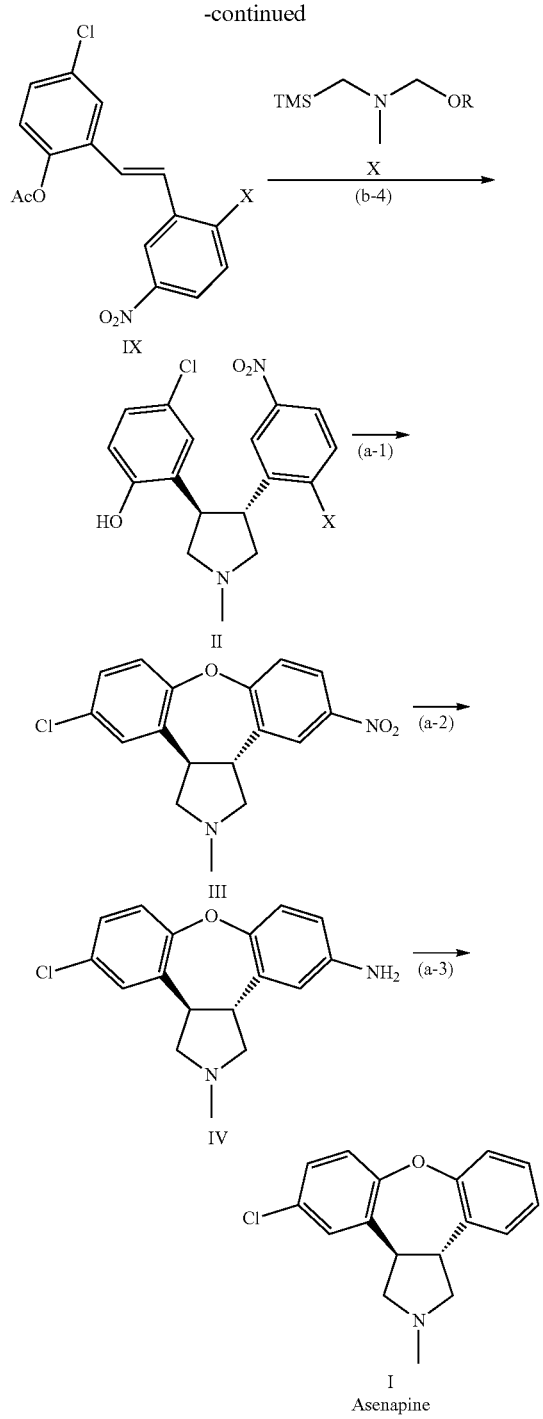

Step (b-1): Synthesis of Compound VI

To a 200 ml reaction flask, 35.2 g Compound V and 63.3 g 48% hydrobromic acid aqueous solution were added, and then 18.4 g sulfuric acid was added dropwise at room temperature. The mixture was warmed to 50° C. and maintained at this temperature for 10 h, cooled to room temperature, and then 100 ml dichloromethane was added. The organic layer was washed with 50 ml of water and 50 ml of sodium carbonate aqueous solution, dried by adding 10 g of sodium sulfate, and filtered. To the organic layer 63.1 g of triethyl phosphite and 8.6 g of anhydrous zinc bromide were added in one portion. The reaction mixture was heated to 40°

C., stirred for 10 h, and cooled slightly, and then 100 ml of water was added to wash it. The water layer was discarded, the organic layer was collected, and the solvent was evaporated under reduced pressure to dryness, yielding Compound VI (54.8 g, 95.0%).

Step (b-2): Synthesis of Compound VIII

Under nitrogen protection, 54.0 g Compound VI was dissolved in 500 ml tetrahydrofuran, to which 30.1 g 5-chlorosalicylaldehyde was added. The mixture was cooled to 0° C., and 39.2 g potassium tert-butoxide was added in portions while maintaining the temperature at 0° C. After the reaction is completed, 300 ml of water and 300 ml of toluene were added. The organic layer was washed with 200 ml of sodium carbonate solution and saturated sodium chloride solution. The organic layer was evaporated to dryness under reduced pressure at 50° C. to obtain Compound VIII (52.9 g, 97.2%).

Step (b-3): Synthesis of Compound IX

Under nitrogen protection, 52.0 g Compound VIII, 17.1 g pyridine, 200 ml toluene were added, to which 21.7 g acetic anhydride was added dropwise at room temperature. Reaction was maintained overnight. The mixture was warmed to 50° C., to which 41 ml water and 13 ml ethanol were added, and the temperature was maintained for 30 min. The mixture was cooled to room temperature, and filtered to obtain product IX (58.2 g, 98.5%).

$^1$H NMR (400 MHz, CDCl$_3$) δ (ppm): 8.48 (d, 1H), 8.07-8.10 (dd, 1H), 8.67-8.68 (d, 1H), 7.57-7.60 (d, 1H), 7.44-7.48 (d, 1H), 7.31-7.34 (dd, 1H), 7.14-7.18 (d, 1H), 7.08-7.10 (d, 1H), 2.41 (s, 3H).

Step (b-4): Synthesis of Compound II 58.0 g Compound IX was dissolved in 500 ml of toluene in the reaction flask, to which 0.5 g trifluoroacetic acid was added. 32.7 g N-(methoxymethyl)-N-methyl-(trimethylsilyl)methylamine was added dropwise within 1 hour, and the mixture was maintained at ambient temperature for 3 h. The organic layer was concentrated under vacuum to obtain an oil. The oil was dissolved in 400 ml of methanol, and potassium hydroxide aqueous solution (10.5 g potassium hydroxide was dissolved in 90 ml water) was added. After 1 h, the pH value was adjusted to 8-9 with 3 N hydrochloric acid. The mixture was stirred for 30 min and filtered. The resulting product was dried under vacuum for 10 h to obtain Compound II (56.0 g, 92.6%).

$^1$H NMR (400 MHz, CDCl$_3$) δ (ppm): 12.39 (s, —OH), 8.26 (s, 1H), 8.04-8.06 (d, 1H), 7.52-7.54 (d, 1H), 7.05-7.06 (d, 1H), 6.81-6.83 (d, 1H), 6.76 (s, 1H), 4.13 (s, 1H), 3.67-3.70 (t, 1H), 3.31 (s, 1H), 3.24-3.26 (d, 1H), 2.95-2.98 (t, 1H), 2.57 (s, 3H), 2.37-2.41 (t, 1H).

$^{13}$C NMR (101 MHz, CDCl$_3$) δ (ppm): 154.75, 147.05, 142.12, 141.12, 131.30, 131.13, 129.44, 128.45, 123.34, 123.02, 122.79, 119.43, 63.23, 61.66, 51.42, 48.24, 39.95.

Step (a-1): Synthesis of Compound III

Under nitrogen protection, 50.0 g Compound II and 250 ml tetrahydrofuran were added to the reaction flask. The mixture was stirred, and then 22.6 g potassium carbonate was added. The resulting mixture was warmed to 50-60° C. and the temperature was maintained for 3 h. The mixture was cooled to ambient temperature, and then 750 ml water was added dropwise. The mixture was stirred for 30 min and filtered. The product was dried under vacuum to obtain Compound III (43.1 g, 95.6%).

$^1$H NMR (400 MHz, CDCl$_3$) δ (ppm): 8.07-8.10 (dd, 1H), 7.98-7.99 (d, 1H), 7.26-7.29 (d, 1H), 7.18-7.21 (m, 1H), 7.13-7.15 (d, 2H), 3.66-3.73 (m, 1H), 3.52-3.60 (m, 1H), 3.30-3.35 (m, 1H), 3.13-3.23 (m, 3H), 2.57 (s, 3H).

$^{13}$C NMR (101 MHz, CDCl$_3$) δ (ppm): 159.71, 153.14, 143.59, 133.89, 132.45, 130.12, 127.88, 126.27, 123.58, 122.39, 121.91, 59.66, 58.35, 45.74, 44.39, 42.97.

MS (ESI): m/z=330.08, [1\4+H]$^+$=331.08.

Step (a-2): Synthesis of Compound IV 42.0 g Compound III was dissolved in 500 ml of methanol, to which 4.0 g of active nickel wet product was added. Air was replaced with vacuum, heated to 60° C., and hydrogen is introduced to react for 6 to 8 h. The mixture was filtered to remove nickel, and the reaction solution was concentrated under vacuum to obtain an oil. The oil was dissolved in 250 ml methanol, and 250 ml water was added with stirring, and the mixture was stirred for 30 min and filtered. The product was dried under vacuum to obtain Compound IV (36.4 g, 95.4%).

Step (a-3): Synthesis of Compound I (Asenapine)

36.0 g of Compound IV was dissolved in 117 g of hypophosphorous acid, cooled to 10 to 20° C., to which 31.2 g of 30% aqueous solution of sodium nitrite was added dropwise, and the addition was completed after 3 to 4 h. After the completion of the addition, the temperature was kept at 10 to 20° C. while the mixture was stirred for 6 to 8 h. 78.0 g of ammonia aqueous solution was added dropwise while maintaining the temperature below 30° C. The pH of the water layer was adjusted to 8-9, to which 156 ml of n-heptane was added. The organic layer was washed with 78 ml of water. The organic layer was evaporated to dryness under reduced pressure at 50° C. to give crude product.

To the crude product, 110 ml of n-heptane and 8.0 ml of toluene were added. After heating to 40 to 50° C. and stirring to dissolve the crude product, the solution was cooled in a rate of 5-10° C. per hour to crystallize. The solution was cooled to 20 to 25° C. and stirred to precipitate the crystal for 1.0 to 1.5 h. After a large amount of solid precipitates, the solution was cooled to −5 to 0° C., and stirred for 1.0 h while maintaining the temperature. The solution was filtered, the crystalline Asenapine was collected, and dried under vacuum at 40 to 45° C. to obtain the compound in crystalline form (30.6 g, 89.5%, HPLC Purity >99%).

$^1$H NMR (400 MHz, CDCl$_3$) δ (ppm): 7.14-7.20 (m, 2H), 7.11 (s, 2H), 7.05-7.09 (m, 3H), 3.58-3.68 (m, 2H), 3.18-3.25 (m, 2H), 3.08-3.16 (m, 2H), 2.55 (s, 3H).

$^{13}$C NMR (101 MHz, CDCl$_3$) δ (ppm): 155.22, 151.14, 134.01, 131.88, 128.91, 127.64, 127.33, 126.79, 126.71, 124.15, 122.35, 120.90, 59.12, 59.00, 44.83, 44.72, 43.25.

MS (ESI): m/z=285.09, [1\4+H]$^+$=286.10.

Example 2

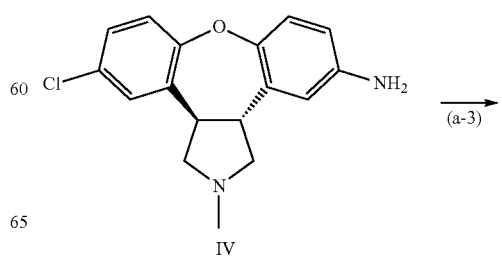

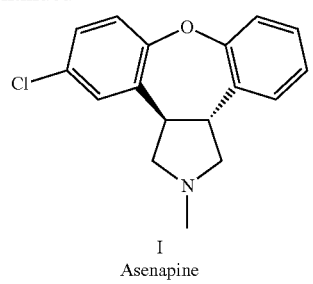

I
Asenapine 73.0 g of Compound IV was dissolved in 220 g of hypophosphorous acid, cooled to 0 to 15° C., to which 64.0 g of 30% aqueous solution of sodium nitrite was added dropwise, and the addition was completed after 2 to 3 h. After the completion of the addition, the temperature was kept at 10 to 20° C. while the mixture was stirred for 5 to 9 h. 160 g of ammonia aqueous solution was added dropwise while maintaining the temperature below 30° C. The pH of the water layer was adjusted to 8-9, to which 300 ml of n-hexane was added. The organic layer was washed with 160 ml of water. The organic layer was evaporated to dryness under reduced pressure at 45 to 50° C. to give crude product.

To the crude product, 230 ml of n-heptane and 17 ml of toluene were added. After heating to 40 to 50° C. and stirring to dissolve the crude product, the solution was cooled in a rate of 5-10° C. per hour to crystallize. The solution was cooled to 20 to 25° C. and stirred to precipitate the crystal for 1.0 to 1.5 h. After a large amount of solid precipitates, the solution was cooled to −5 to 0° C., and stirred for 1.0 h while maintaining the temperature. The solution was filtered, the crystalline Asenapine was collected, and dried under vacuum at 40 to 45° C. to obtain the compound in crystalline form (63.3 g, 91.2%, HPLC Purity >99%).

Example 3

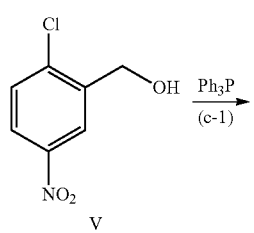

V

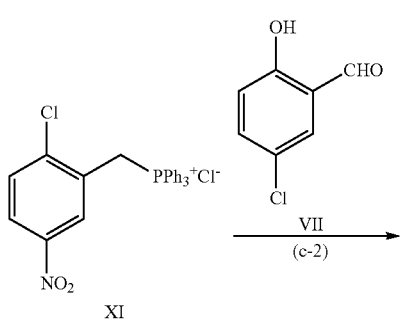

XI

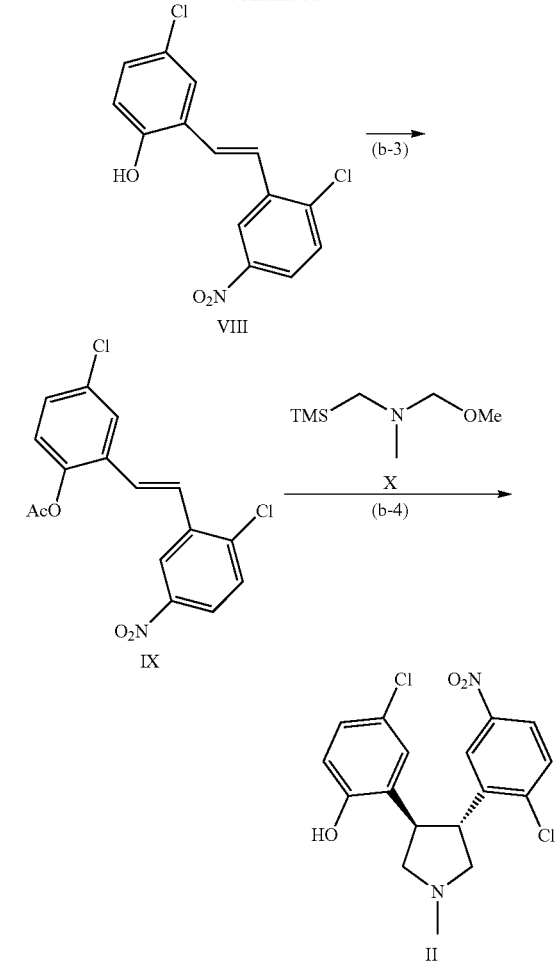

Step (c-1): Synthesis of Compound XI
In a 250 ml reaction flask, 50.0 g Compound V and 75.0 g 48% hydrobromic acid aqueous solution were added, to which 14.0 g sulfuric acid was added dropwise at room temperature. The reaction mixture was warmed to 60° C. and the temperature was maintained for 13 h. The reaction mixture was cooled to room temperature, to which 100 ml toluene was added. The organic layer was washed sequentially with 35.0 g water and 28.0 g of 2.5% sodium carbonate aqueous solution. The solution was kept standing and layers were separated. 65.2 g triphenylphosphine was added to the organic layer. The resulting mixture was stirred at 60° C. for 10 h, then cooled to ambient temperature, and filtered to give Compound XI (118.8 g, 95.2%).

Step (c-2): Synthesis of Compound VIII
Under nitrogen protection, 102.4 g of Compound XI was dissolved in 1000 ml of tetrahydrofuran, and 37.4 g of 5-chlorosalicylaldehyde was added. 15.8 g of pyridine was added dropwise. After the reaction was completed, 600 ml water and 600 ml hexane were added. The organic layer was washed with 400 ml of sodium carbonate solution and with saturated sodium chloride solution. The organic layer was evaporated to dryness under reduced pressure at 50° C., and Compound VIII (62.8 g, 92.6%) was separated by column chromatography.

Step (b-3): Synthesis of Compound IX
Under nitrogen protection, 60.0 g Compound VIII, 21.5 g triethylamine and 230 ml tetrahydrofuran were added, to which 33.4 g acetic anhydride was added dropwise at 15 to 30° C. The reaction was kept overnight. The reaction mixture was heated to 45° C., to which 46 ml water and 15 ml ethanol was added. The temperature was maintained for 30 min. The mixture was cooled to room temperature, and filtered to obtain product IX (66.8 g, 98.0%).

Step (b-4): Synthesis of Compound II 65.0 g of Compound IX was dissolved in 540 ml of tetrahydrofuran in a reaction flask, to which 1.0 g trifluoroacetic acid was added. 37.0 g of N-(methoxymethyl)-N-methyl-(trimethylsilyl)methylamine was added dropwise within 1 hour. The reaction mixture was kept at ambient temperature for 3 h. The organic layer was concentrated under vacuum to obtain an oil. The oil was dissolved in 435 ml of ethanol. Aqueous solution of potassium hydroxide (13.7 g potassium hydroxide was dissolved in 117 ml water) was added. After 1 h, the pH was adjusted to 8-9 with 3 N hydrochloric acid. The mixture was stirred for 30 min and filtered. The product was dried under vacuum for 11 h to obtain Compound II (62.4 g, 92.0%).

Example 4: Preparation Method I of the Crystal of Asenapine Having Formula I

To 60.0 g Asenapine crude product, 180 ml of n-heptane and 15 ml of toluene were added. After heating to 35 to 45° C. and stirring to dissolve the crude product, the solution was cooled in a rate of 5-10° C. per hour to crystallize. The solution was cooled to 15 to 25° C. and stirred for 1.0 h while maintaining the temperature. Subsequently, the solution was cooled to −20 to −10° C. and stirred for 1.0 h while maintaining the temperature. The solution was filtered, the crystalline Asenapine was collected, and dried under vacuum at 35 to 45° C. to obtain Asenapine of formula I in crystalline form (55.2 g, 92.0%, HPLC Purity >99%).

Example 5: Preparation Method II of the Crystal of Asenapine Having Formula I 300 g of ethanol was added to 95.0 g of crude Asenapine. The mixture was warmed up to 40-50° C. to dissolve the crude product. Then the temperature was controlled at 30-40° C. 45 g of purified water was added dropwise. The solution was cooled to 20-25° C., and the temperature was maintained to crystallize for 1.0 to 1.5 h. Then the solution was slowly cooled to 0 to 5° C., and stirred for 1 h while maintaining the temperature. The solution was filtered. The resulting solid was rinsed with an appropriate amount of ethanol aqueous solution, filtered to dryness, and wet product was obtained. The product was dried under vacuum at 50 to 60° C. to obtain Asenapine of formula I in crystalline form (91.4 g, 96.2%, HPLC Purity >99%).

Example 6: Preparation Method III of the Crystal of Asenapine Having Formula I

At room temperature, 400 g of hexane was added to 400 g of 3.0% sodium hydroxide aqueous solution, and then 84.0 g of Asenapine maleate was added in portions. After the mixture was stirred to dissolve, the layers were separated. The aqueous layer was extracted with 150 g of hexane. The organic layers were combined and washed with 2×150 g water. The organic layer was concentrated to dryness under reduced pressure. 200 g of hexane and 20 g of ethyl acetate were added to the reaction system. The mixture was warmed to 45 to 55° C. and stirred to dissolve. The solution was cooled to 15 to 25° C., and the temperature was maintained to crystallize for 1.5 h. Then the solution was cooled to −15 to −10° C., and filtered. The product was collected, and dried in vacuum at 35 to 45° C., to obtain Asenapine of formula I in crystalline form (69.3 g, 93.1%, HPLC Purity >99%).

The invention claimed is:

1. A compound of formula II:

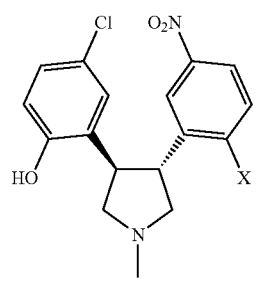

wherein X is F, Cl, Br or I.

2. A method for preparing the compound of formula II according to claim 1, comprising the following steps:

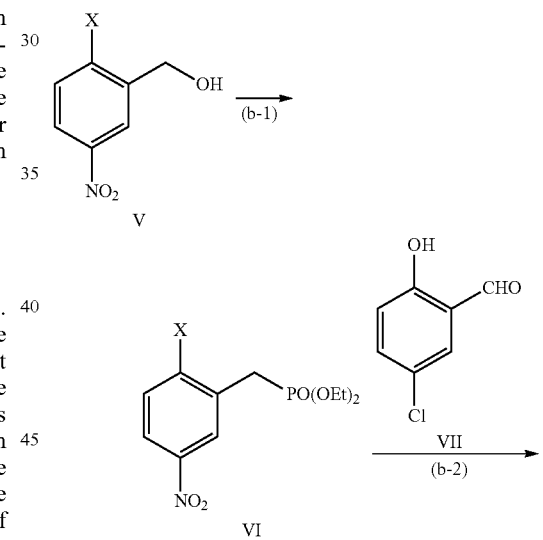

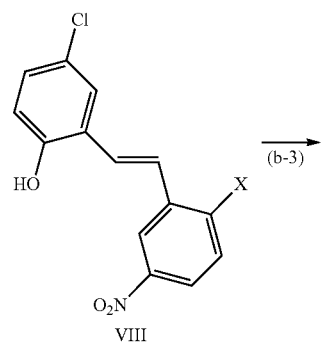

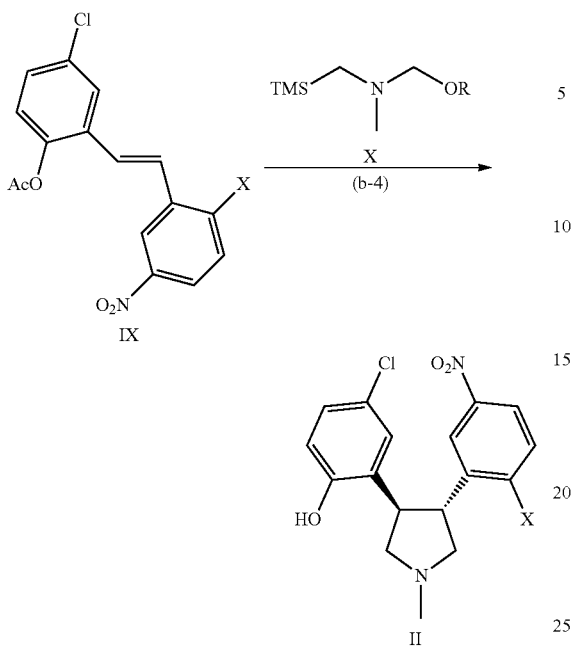

wherein X is F, Cl, Br or I,

Step (b-1): Compound (V) is subjected to the action of sulfuric acid and hydrohalogen acid, thereby replacing the hydroxy group in its structure with a halogen atom, and then is reacted with triethyl phosphite under the catalysis of Lewis acid in an aprotic organic solvent to yield Intermediate VI, Step (b-2): Intermediate VI is reacted with 5-chlorosalicylaldehyde VII under basic condition through Horner-Wadsworth-Emmons reaction to obtain Intermediate VIII, Step (b-3): Intermediate VIII is acetylated with acetic anhydride under basic condition to obtain Intermediate IX, and Step (b-4): Intermediate IX is reacted with N-(alkoxymethyl)-N-methyl-(trimethylsilyl)methylamine (X) under the catalysis of trifluoroacetic acid to perform Huisgen cycloaddition reaction, to obtain the compound of formula II, wherein R is $C_{1-6}$ alkyl.

3. The method according to claim 2, characterized in that, in step (b-1), the hydrohalogen acid used is selected from hydrofluoric acid, hydrochloric acid, hydrobromic acid or hydroiodic acid; the Lewis acid is $FeCl_2$, $FeCl_3$, $FeBr_3$, $ZnCl_2$, $ZnBr_2$ or $InBr_2$; the aprotic organic solvent is selected from dichloromethane, chloroform, tetrahydrofuran, methyltetrahydrofuran, benzene, toluene, xylene, chlorobenzene, or a mixture of two or more thereof.

4. The method according to claim 2, characterized in that, in step (b-2), the base used is selected from lithium hydroxide, sodium hydroxide, potassium hydroxide, lithium carbonate, sodium carbonate, potassium carbonate, sodium bicarbonate, potassium bicarbonate, potassium tert-butoxide, or sodium tert-butoxide.

5. The method according to claim 2, characterized in that, in the compound of formula X in step (b-4), R is $C_{1-4}$ alkyl.

6. A method for preparing the compound of formula II according to claim 1, comprising the following steps:

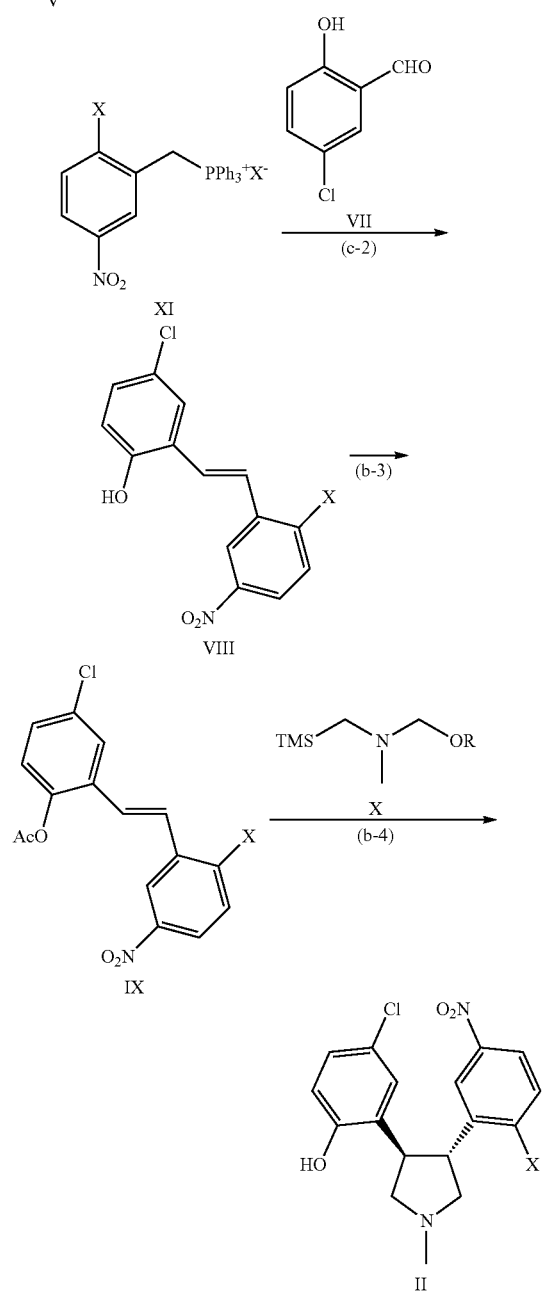

wherein X is F, Cl, Br or I,

Step (c-1): Compound (V) is subjected to the action of sulfuric acid and hydrohalogen acid, thereby replacing the hydroxy group in its structure with a halogen atom, and then is reacted with triphenylphosphine in an aprotic organic solvent to obtain Intermediate XI, Step (c-2): Intermediate XI is reacted with 5-chlorosalicylaldehyde VII under basic condition through Witting reaction to yield Intermediate VIII, Step (b-3): Intermediate VIII is acetylated with acetic anhydride under basic condition to obtain Intermediate IX, and Step (b-4): Intermediate IX is reacted with N-(alkoxymethyl)-N-methyl-(trimethylsilyl)methylamine (X) under the catalysis of trifluoroacetic acid to perform Huisgen cycloaddition reaction, to obtain the compound of formula II, wherein R is $C_{1-6}$ alkyl.

7. The method according to claim 6, characterized in that, in step (c-1), the hydrohalogen acid used is selected from hydrofluoric acid, hydrochloric acid, hydrobromic acid or hydroiodic acid; and the aprotic organic solvent used is selected from dichloromethane, chloroform, tetrahydrofuran, methyltetrahydrofuran, benzene, toluene, xylene, chlorobenzene, or a mixture of two or more thereof.

8. The method according to claim 6, characterized in that, in step (c-2), the base used is selected from inorganic bases or organic bases.

9. The method according to claim 8, characterized in that the inorganic bases are selected from lithium hydroxide, sodium hydroxide, potassium hydroxide, sodium carbonate, potassium carbonate, sodium tert-butoxide, or potassium tert-butoxide; and the organic bases are selected from triethylamine, pyridine, p-dimethylaminopyridine, or diisopropylethylamine.

\* \* \* \* \*